US012616854B2

(12) United States Patent
Styron et al.

(10) Patent No.: US 12,616,854 B2
(45) Date of Patent: May 5, 2026

(54) MONITORING AND CONTROL OF NEUTRON BEAM SYSTEMS

(71) Applicant: TAE Life Sciences, LLC, Foothill Ranch, CA (US)

(72) Inventors: Jedediah Styron, Wildomar, CA (US); Jonathan David McCoy, Sunnyvale, CA (US); Charles Leon Lee, Irvine, CA (US); Matthew Alan Core, Reno, NV (US)

(73) Assignee: TAE Life Sciences, LLC, Foothill Ranch (CA)

( * ) Notice: Subject to any disclaimer, the term of this patent is extended or adjusted under 35 U.S.C. 154(b) by 123 days.

(21) Appl. No.: 18/239,568

(22) Filed: Aug. 29, 2023

(65) Prior Publication Data

US 2024/0066323 A1 Feb. 29, 2024

Related U.S. Application Data

(60) Provisional application No. 63/504,981, filed on May 30, 2023, provisional application No. 63/402,286, filed on Aug. 30, 2022.

(51) Int. Cl.
*A61N 5/10* (2006.01)
*G01T 3/00* (2006.01)
*G01T 7/00* (2006.01)

(52) U.S. Cl.
CPC ......... *A61N 5/1071* (2013.01); *A61N 5/1067* (2013.01); *G01T 7/005* (2013.01);
(Continued)

(58) Field of Classification Search
CPC ............................ A61N 6/1067; A61N 6/1071
See application file for complete search history.

(56) References Cited

U.S. PATENT DOCUMENTS 5,903,622 A 5/1999 Yoon et al.
10,286,229 B2 5/2019 Baltes et al.
(Continued)

FOREIGN PATENT DOCUMENTS

EP 3342459 2/2020

OTHER PUBLICATIONS

International Search Report and Written Opinion in International Appln. No. PCT/US2023/031417, mailed on Jan. 17, 2024, 12 pages.
(Continued)

*Primary Examiner* — Casey Bryant
(74) *Attorney, Agent, or Firm* — ALSTON & BIRD LLP

(57) ABSTRACT

A method for monitoring and controlling neutron beams includes performing a calibration process for a monitoring dosimeter at a first set of conditions for directing a neutron beam towards an object location, the neutron beam being emitted from a neutron-generating target in response to an incident charged particle beam, the process comprising: obtaining data indicating a first neutron flux measured by the monitoring dosimeter between the monitoring dosimeter and the object location, the monitoring dosimeter offset from the axis by a distance equal to or greater than the beam radius; obtaining data indicating a second neutron flux measured by a reference dosimeter between the target and the object location; storing calibration data including a correlation between the first neutron flux and the second neutron flux; and based on the calibration data, using the monitoring dosimeter to monitor neutron flux incident on a patient during boron neutron capture therapy treatment.

16 Claims, 14 Drawing Sheets

900

OBTAINING DATA INDICATING A FIRST NEUTRON FLUX MEASURED BY A DOSIMETER OF A SYMMETRY MONITORING SYSTEM 902

OBTAINING DATA INDICATING A SECOND NEUTRON FLUX MEASURED BY A MONITORING DOSIMETER 904

STORING CALIBRATION DATA INCLUDING A CORRELATION BETWEEN THE FIRST NEUTRON FLUX AND THE SECOND NEUTRON FLUX 906

USING THE CALIBRATION DATA AND THE NEUTRON FLUX MEASURED BY THE MONITORING DOSIMETER TO DETERMINE AN EXPECTED NEUTRON FLUX MEASURED BY THE DOSIMETER OF THE SYMMETRY MONITORING SYSTEM 908

BASED ON THE EXPECTED NEUTRON FLUX MEASURED BY THE DOSIMETER OF THE SYMMETRY MONITORING SYSTEM, MONITORING THE NEUTRON FLUX INCIDENT ON THE PATIENT 910

(52) U.S. Cl.
CPC     *A61N 2005/1087* (2013.01); *A61N 2005/109*
(2013.01); *G01T 3/00* (2013.01)

(56)                    References Cited

U.S. PATENT DOCUMENTS

| | | | |
|---|---|---|---|
| 2003/0142776 A1* | 7/2003 | Shibazaki | G01T 3/00 |
| | | | 376/154 |
| 2018/0236265 A1* | 8/2018 | Mukawa | G01V 5/234 |
| 2021/0008391 A1 | 1/2021 | Niimi et al. | |
| 2021/0260409 A1 | 8/2021 | Liu | |
| 2022/0078900 A1* | 3/2022 | Vekselman | H05H 9/02 |
| 2023/0213668 A1* | 7/2023 | Imaizumi | G21C 17/108 |
| | | | 250/370.05 |
| 2024/0066319 A1* | 2/2024 | Lin | A61N 5/1064 |

OTHER PUBLICATIONS

Naito, "Introduction to accelerators for boron neutron capture therapy," Therapeutic Radiology and Oncology, Nov. 2018, 2:54, 13 pages.

* cited by examiner

100

100

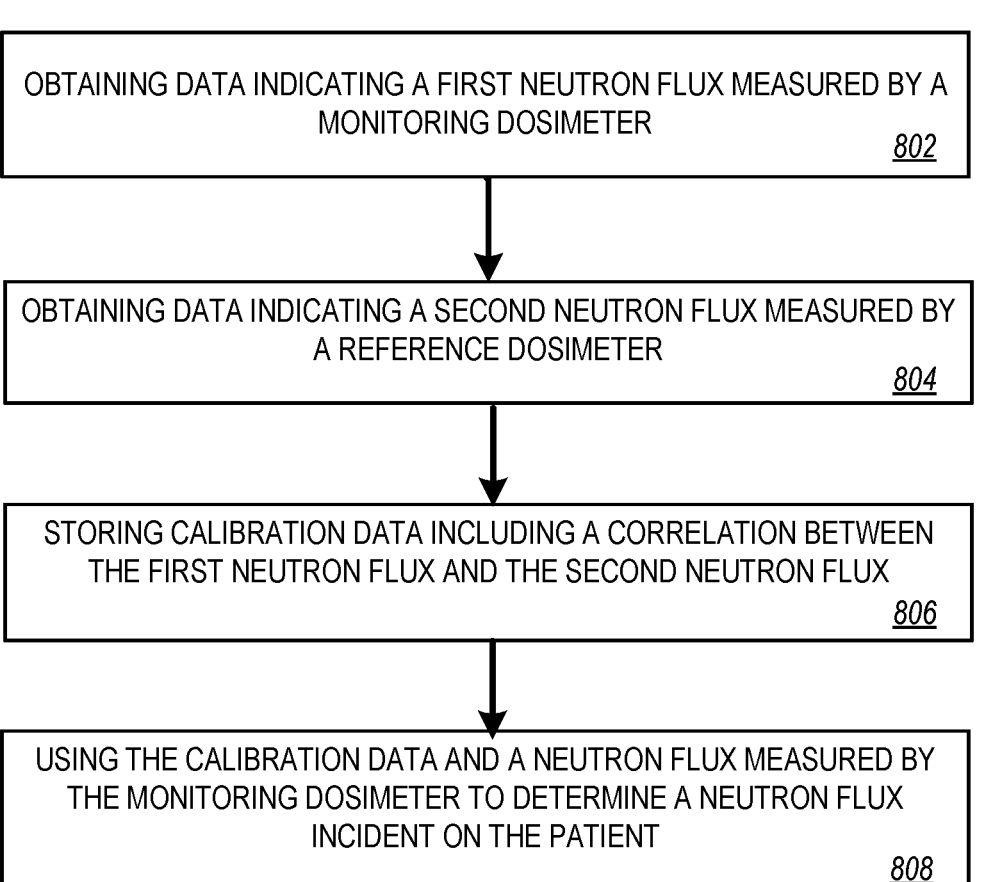

OBTAINING DATA INDICATING A FIRST NEUTRON FLUX MEASURED BY A MONITORING DOSIMETER
                                                                                    _802_

OBTAINING DATA INDICATING A SECOND NEUTRON FLUX MEASURED BY A REFERENCE DOSIMETER
                                                                                    _804_

STORING CALIBRATION DATA INCLUDING A CORRELATION BETWEEN THE FIRST NEUTRON FLUX AND THE SECOND NEUTRON FLUX
                                                                                    _806_

USING THE CALIBRATION DATA AND A NEUTRON FLUX MEASURED BY THE MONITORING DOSIMETER TO DETERMINE A NEUTRON FLUX INCIDENT ON THE PATIENT
                                                                                    _808_

FIG. 8

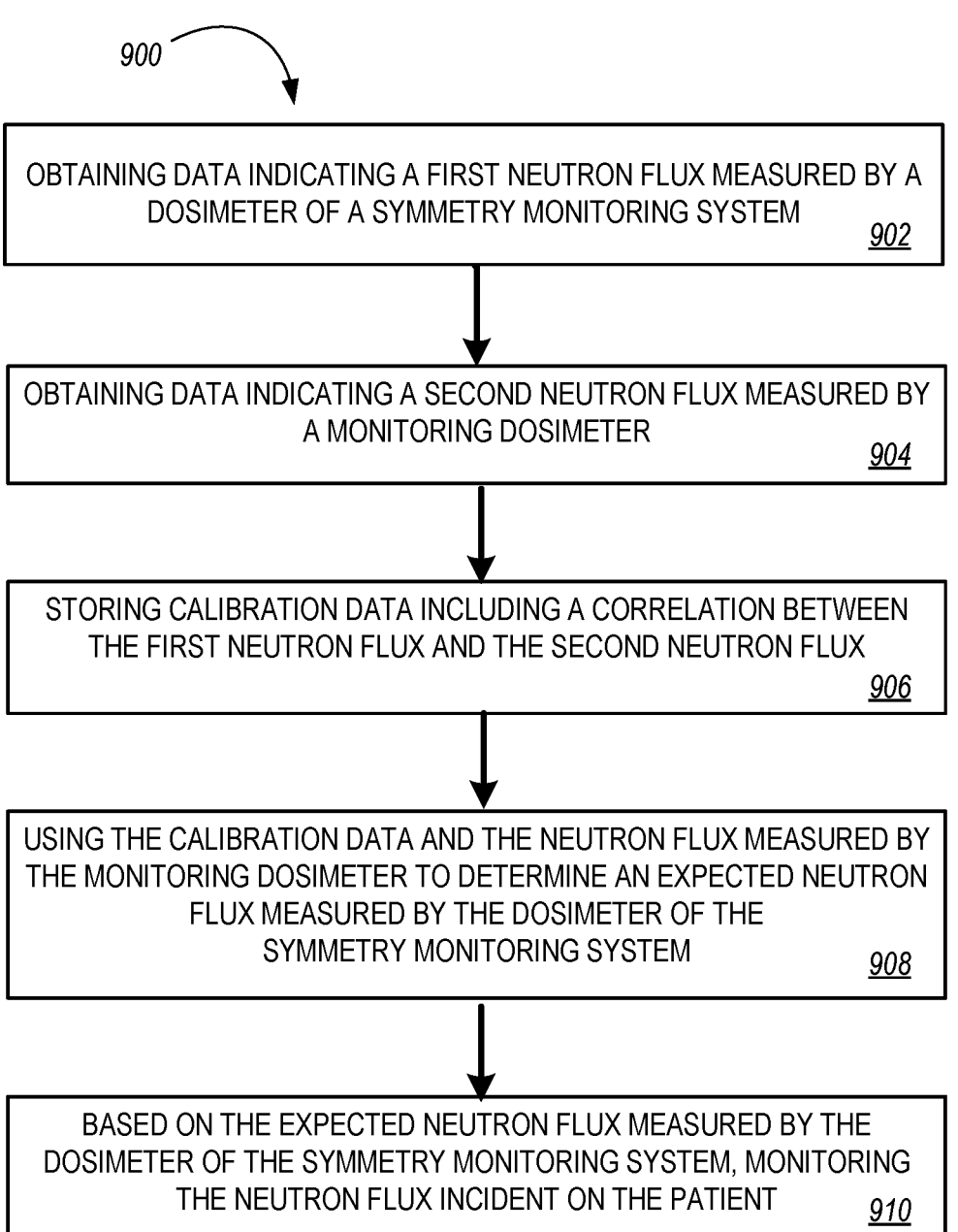

900

OBTAINING DATA INDICATING A FIRST NEUTRON FLUX MEASURED BY A DOSIMETER OF A SYMMETRY MONITORING SYSTEM          902

OBTAINING DATA INDICATING A SECOND NEUTRON FLUX MEASURED BY A MONITORING DOSIMETER          904

STORING CALIBRATION DATA INCLUDING A CORRELATION BETWEEN THE FIRST NEUTRON FLUX AND THE SECOND NEUTRON FLUX          906

USING THE CALIBRATION DATA AND THE NEUTRON FLUX MEASURED BY THE MONITORING DOSIMETER TO DETERMINE AN EXPECTED NEUTRON FLUX MEASURED BY THE DOSIMETER OF THE SYMMETRY MONITORING SYSTEM          908

BASED ON THE EXPECTED NEUTRON FLUX MEASURED BY THE DOSIMETER OF THE SYMMETRY MONITORING SYSTEM, MONITORING THE NEUTRON FLUX INCIDENT ON THE PATIENT          910

OBTAINING A MEASURE OF A NEUTRON BEAM DURING A BNCT
TREATMENT

*1002*

DETERMINING A DIFFERENCE BETWEEN THE MEASURE OF THE
NEUTRON BEAM AND AN EXPECTED MEASURE

*1004*

ADJUSTING A DURATION OF THE BNCT TREATMENT BASED ON THE
DIFFERENCE BETWEEN THE MEASURE OF THE NEUTRON BEAM AND
THE EXPECTED MEASURE OF THE NEUTRON BEAM

*1006*

*1100*

OBTAINING A MEASURE OF A NEUTRON BEAM OUTPUT BY
A NEUTRON BEAM SYSTEM     *1102*

DETERMINING A DIFFERENCE BETWEEN THE MEASURE OF THE
NEUTRON BEAM AND AN EXPECTED MEASURE     *1104*

OBTAINING A VALUE OF A PARAMETER OF
THE NEUTRON BEAM SYSTEM     *1106*

DETERMINING A DIFFERENCE BETWEEN THE VALUE OF
THE PARAMETER AND AN EXPECTED VALUE     *1108*

ADJUSTING A SETTING OF THE NEUTRON BEAM SYSTEM
    *1110*

1

MONITORING AND CONTROL OF NEUTRON BEAM SYSTEMS

CROSS-REFERENCE TO RELATED APPLICATIONS

This application claims the benefit of the U.S. Provisional Patent Application No. 63/402,286 filed Aug. 30, 2022, and of the U.S. Provisional Patent Application No. 63/504,981 filed May 30, 2023, which are incorporated herein by reference in their entirety.

FIELD

The subject matter described herein relates generally to systems, devices, and methods for monitoring neutron radiation and/or controlling neutron beams.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. The boron compound allows for efficient uptake by a variety of cell types and selective drug accumulation at target sites, such as tumor cells. Boron loaded cells can be irradiated with neutrons (e.g., in the form of a neutron beam). The neutrons react with the boron to eradicate the tumor cells.

Neutron beams for BNCT can be generated through various techniques. In some cases, this is accomplished by colliding protons with a neutron generating target containing lithium-7 to generate neutrons according to the Li-7(p,n) Be-7 nuclear reaction. In other cases, the neutrons can be generated by impacting a target containing beryllium-9 with a proton beam (Be-9(p,n)B-9) or deuteron beam (Be-9(d,n) B-10) at different energies. Still other techniques can be used. The charged particles react with nuclei in the target to emit a beam of raw neutrons that can be used for BNCT.

Generally, a BNCT treatment plan dose is correlated to the charged particle current, or number of charged particles incident on the neutron generating target, which is not a direct measure of the number of neutrons produced. For example, if the charged particle beam (in this case protons) veers off the target region onto the substrate the measured current will be constant even though no neutrons are being produced. In addition, the charged particle current is unable to monitor target conditions, e.g., changes to the lithium target via nuclear depletion, mechanical failure, or chemical reactions. Therefore, measuring the charged particle current as a surrogate to neutrons is valid if the charged particle beam does not deviate from the target and the target material remains a uniform thickness, composition, and density throughout the treatment.

For these and other reasons, needs exist for improved systems, devices, and methods for monitoring neutron radiation and/or controlling neutron beams.

SUMMARY

The subject matter described herein relates generally to systems, devices, and methods for monitoring and controlling neutron beams. Embodiments of a neutron beam monitoring and control system are described in an example context of a BNCT system configured to output a neutron beam in an epithermal energy range. The embodiments described herein are usable in non-BNCT applications as well.

The present subject matter can be used to provide a neutron measurement that provides a real-time monitor of the treatment conditions. In addition, this subject matter permits active correction, and can reduce the impact of time-consuming calibrations for each treatment plan on the BNCT treatment facility throughput. The present subject matter can permit for a direct relationship to be established between the desired treatment plan dose and a neutron measurement. Also provided are methods to monitor real-time fluctuations in the neutron rate and methods to control the precise delivery of a specific quantity and distribution of dose at the desired location.

BRIEF DESCRIPTION OF DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 8 shows a flow diagram of an example embodiment of a process for neutron beam monitoring and control using a neutron monitoring dosimeter in accordance with the present disclosure.

FIG. 9 shows a flow diagram of an example embodiment of a process for neutron beam monitoring and control using a symmetry monitoring system in accordance with the present disclosure.

DETAILED DESCRIPTION

Figure 1A:
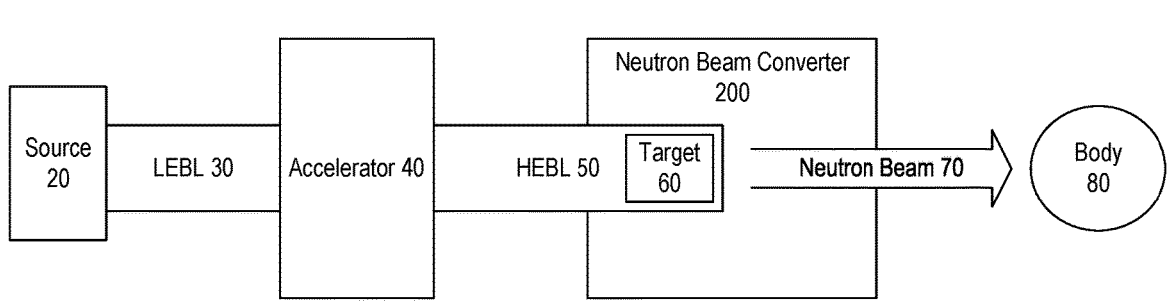
FIG. 1A shows a schematic view depicting an example of a neutron beam system in accordance with the present disclosure.

This disclosure is not limited to the particular embodiments described. The terminology used herein is for the purpose of describing particular embodiments only and is not intended to be limiting since the scope of the present disclosure will be limited only by the appended claims.

The term "particle" is used broadly herein and, unless otherwise limited, can be used to describe an electron, a proton (or H+ ion), or a neutron, as well as a species having more than one electron, proton, and/or neutron (e.g., other ions, atoms, and molecules).

Example embodiments of systems, devices, and methods are described herein for neutron beam monitoring and control, which can be used in combination with a neutron beam system (e.g., including a reactor or a particle accelerator). The embodiments described herein can be used with any type of neutron beam system in which neutron beam conversion or modification is desired. Embodiments herein can be used in numerous applications, an example of which is a neutron beam system for generation of a neutron beam for use in BNCT. BNCT uses a beam of neutrons (e.g., typically an epithermal beam with an energy spectrum between one electronvolt (eV) and thirty kiloelectronvolts (keV), in some examples, or between one eV and 10 keV in certain other examples) for cancer treatment. As mentioned, the neutrons are often generated from nuclear reactions of charged particles (e.g., a proton beam) colliding with either a beryllium or a lithium target device. The generated neutron beam has a broad range of energies and is emitted in a variety of directions. Thus, the target can be contained within a larger neutron beam converter (NBC) that functions to convert the generated neutron beam into a primarily forward directed beam within the desired epithermal energy range, which is then output to a human or animal patient.

The example embodiments of neutron beam monitoring and control systems described herein are not intended to be viewed in isolation from each other. All features, elements, components, and functions described with respect to any converter embodiment provided herein are intended to be freely combinable and substitutable with those from any other converter embodiment. If a certain feature, element, component, and function is described with respect to only one converter embodiment, then that that feature, element, component, and function can be used with every other converter embodiment described herein unless explicitly stated otherwise. This paragraph therefore serves as antecedent basis and written support for the introduction of claims, at any time, that combine features, elements, components, and functions from different converter embodiments, or that substitute features, elements, components, and functions from one converter embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

For ease of description, the embodiments described herein will be done so in the context of generating a neutron beam for use in BNCT, where the neutrons are generated by colliding protons with a lithium-7 target, although the embodiments are not limited to such a generation method. The embodiments can be applied to other applications that generate significant neutron radiation, even those outside of BNCT applications utilizing different energy ranges.

FIG. 1A illustrates a schematic view of an example embodiment of a system 100 for use in BNCT, in accordance with the present disclosure. System 100 is configured to create a charged particle beam and propagate it to a target 60 to generate a neutron beam 70 that is directed towards a patient body 80 to be irradiated. Beam system 100 includes a charged particle source 20, a low-energy beamline (LEBL) 30, an accelerator 40, and a high-energy beamline (HEBL) 50. Source 20 is configured to generate the charged particle beam, which is output to LEBL 30. LEBL 30 is configured to transport the beam from source 20 to accelerator 40. Accelerator 40 is configured to accelerate the charged particle beam to a higher energy. HEBL 50 extends from the accelerator 40 to target 60 housed within a target assembly portion of HEBL 50. HEBL 50 transfers the charged particle beam from an output of accelerator 40 to target 60, where it is converted to neutron beam 70.

Neutron beam converter (NBC) 200 is positioned close to and around target 60 to perform various functions on the neutrons of beam 70 emanating from target 60. These functions include reducing the energy of generated neutrons from energies above the desired range to within the desired range, focusing the generated neutrons in a forward-facing direction towards the patient, removing generated neutrons that are outside the desired range, and removing other radiation byproducts (e.g., such as photons) at energy levels that are undesirable. The desired neutron energy range can vary based on the application. For the BNCT applications described herein, the desired energy range can be, for example, one eV to ten keV, or one eV to thirty keV, with the neutron distribution peaking near the upper end of the desired range. For example, a one eV to 30 keV beam can be configured to output at least 90% of the neutrons in that energy range with a peak neutron distribution and an average energy between 10 keV and 30 keV. By way of another example, a one eV to ten keV beam can be configured to output at least 90% of the neutrons in that energy range with a peak neutron distribution and an average energy between three keV and 10 keV. For convenience these ranges will be described as epithermal energy ranges. Neutrons at energies beneath these ranges will be referred to as thermal neutrons (e.g., beneath one eV), and those above these ranges will be referred to as fast neutrons (e.g., above 30 keV).

5

6

Figure 1B:
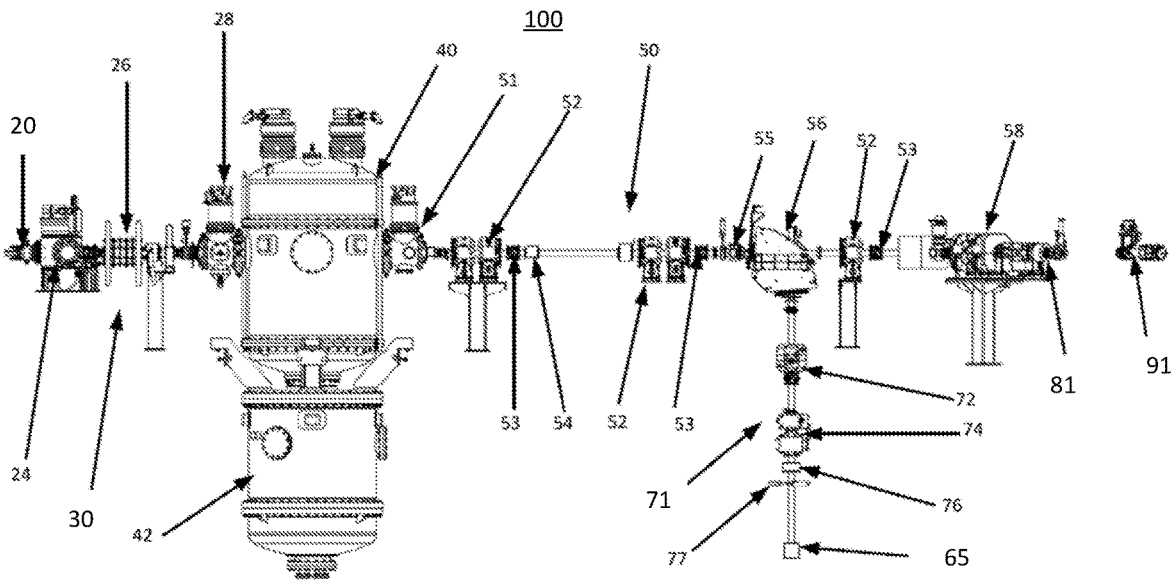
FIG. 1B shows a schematic view depicting an example of a neutron beam system for use in BNCT in accordance with the present disclosure.

FIG. 1B is a schematic view illustrating an example embodiment of beam system 100 configured as a neutron beam system for use in BNCT. Beam system 100 includes a pre-accelerator system 26 forming at least a portion of LEBL 30, where pre-accelerator system 26 serves as a charged particle beam injector. System 100 includes a high voltage (HV) tandem accelerator 40 coupled to LEBL 30, and HEBL 50 extending from tandem accelerator 40 to a target 60, as described with reference to FIG. 1A.

LEBL 30 transfers a negative ion beam (e.g., H– ions) from ion source 20, through pre-accelerator 26 which boosts the energy level of the ion beam and converges the ion beam, to an input (e.g., an input aperture) of accelerator 40. Accelerator 40 is powered by a high voltage power supply 42 coupled thereto. Accelerator 40 includes a vacuum tank, a charge-exchange tube, accelerating electrodes, and a high voltage feedthrough. Accelerator 40 can, in some implementations, accelerate a hydrogen ion beam to produce a proton beam with an energy generally equal to twice the voltage applied to the accelerating electrodes positioned within accelerator 40. The energy level of the proton beam can be achieved by accelerating the beam of negative hydrogen ions from the input of accelerator 40 to the innermost high-potential electrode, stripping two electrons from each ion, and then accelerating the resulting protons downstream by the same voltages encountered in reverse order.

HEBL 50 can transfer the proton beam from the output of accelerator 40 to the neutron-generating target 60 positioned at the end of a branch 71 of the beamline extending into a patient treatment room. Beam system 100 can be configured to direct the proton beam to one or more targets 60 and associated target areas. In some implementations, HEBL 50 includes multiple (e.g., three) branches 71, 81, and 91 configured to extend to multiple different patient treatment rooms, with each branch terminating in a target 60 and NBC 200. HEBL 50 includes a pumping chamber 51, quadrupole magnets 52 and 72 to prevent de-focusing of the beam, dipole or bending magnets 56 and 58 to steer the beam towards one or more targets, beam correctors 53, diagnostics such as current monitors 54 and 76, a fast beam position monitor 55 section, and a scanning magnet 74 for branch 71. Branches 81 and 91 can contain components similar to branch 71.

The design of HEBL 50 depends on the configuration of the treatment facility (e.g., a single-story treatment facility, a two-story treatment facility, and the like). The beam can be delivered to target 60 (e.g., positioned near a treatment room having a patient 80) with the use of the bending magnet 56. Quadrupole magnets 72 can be included to then focus the beam to a certain size at target 60. The beam can pass one or more scanning magnets 74, which provide lateral movement of the beam onto the target surface in a desired pattern (e.g., spiral, curved, stepped in rows and columns, combinations thereof, and others). The beam lateral movement can enable generation of smooth and even time-averaged distribution of the proton beam on the target 60, preventing overheating of the target and making the particle (e.g., neutron) generation as uniform as possible within the target (e.g., neutron generating layer 121 of FIG. 2A).

Scanning magnets 74 can be configured to direct the beam to a current monitor 76, which measures beam current. The beam current value can be used to operate a safety interlock. The target assembly 65 containing target 60 can be physically separated from the high-energy beamline volume with a valve 77. A function of valve 77 is to separate the vacuum volume of the beamline from the target 60 during removal of a used target and loading of a new target. In some implementations, instead of being bent by 90 degrees by a bending magnet 56, the beam can be directed straight to one or more quadrupole magnets 52 located in the horizontal beamline. The beam could be bent by another bending magnet 58 to a preset angle, depending on a setting requirement (e.g., location of a patient or a room configuration). In some implementations, bending magnet 58 can be arranged at a split in the beamline and can be configured to direct the beam in one of two directions for two different treatment rooms located on the same floor of a medical facility.

System 100 as described with respect to FIG. 1B is one example of different configurations that can be used to generate charged particle and neutron beams. Different configurations of system 100 can utilize accelerators other than electrostatic tandem accelerators, and can utilize targets that are either fixed or rotating. The embodiments of NBC 200 described herein are not limited to use with any one type of neutron beam generating system.

Figure 2A:
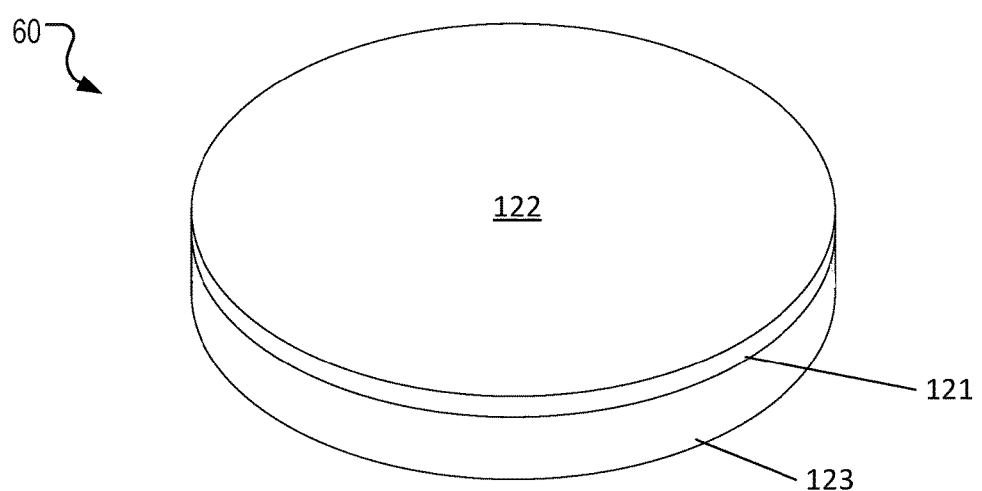
FIG. 2A shows a perspective view depicting an example of a neutron generating target in accordance with the present disclosure.

FIG. 2A is a perspective view of an example embodiment of a target 60. In this embodiment target 60 has a neutron generating layer 121 with a charged particle receiving face surface 122. Neutron generating layer 121 is positioned on or in proximity to a substrate 123. In some cases, layer 121 is covered with one or more other layers for protection. Layer 121 can also have one or more underlying layers between layer 121 and substrate 123, e.g., to resist blister formation. A charged particle beam, such as a proton beam, incident upon face 122, passes into target 60 and causes layer 121 to undergo a reaction that generates neutrons. This is the Li-7(p,n)Be-7 nuclear reaction in the case where neutron generating layer 121 is composed of lithium-7. Neutron generating layer 121 can alternatively be beryllium-9, and neutrons can be generated with a proton beam (Be-9(p,n)B-9) or deuteron beam (Be-9(d,n)B-10) at different energies. Substrate 123 can be a material with excellent thermal conductivity, such as copper or aluminum, to assist in removal of the heat generated by the reactions.

Figure 2B:
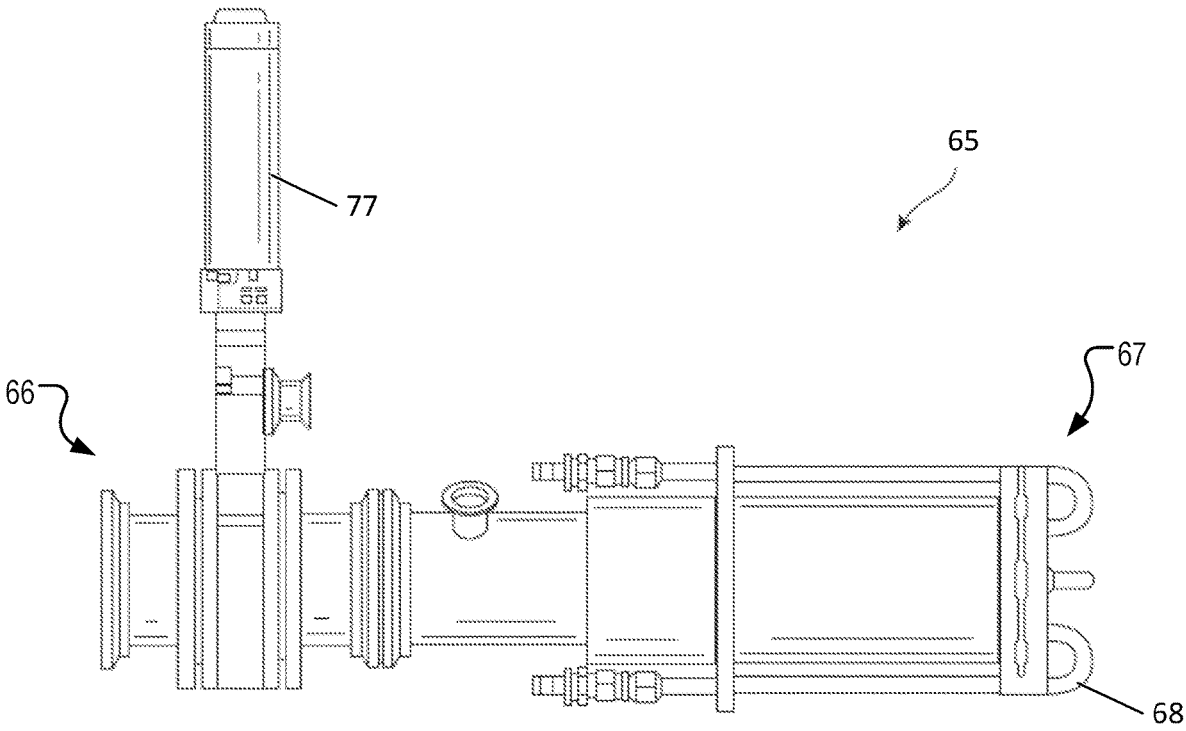
FIG. 2B shows a side view depicting an example of an assembly for housing a neutron generating target in accordance with the present disclosure.

FIG. 2B is a side view of an example embodiment of a target assembly 65 that can form a terminal portion of HEBL 50. Target 60 (not shown) can be contained within assembly 65 at or near end 67. The charged particle beam enters assembly 65 at end 66 and travels to the opposite end 67 where it impacts target 60. Various cooling channels 68 are routed to and from end 67 for the insertion and removal of coolant used to regulate the temperature of target 60 during use. Numerous sensors can be included to monitor temperature and radioactivity of and around assembly 65. Also shown is valve 77 in the example form of a gate valve. End 67 of assembly 65 is inserted into an aperture 205 (FIG. 3A) within NBC 200 where it remains during BNCT procedures. Assembly 65 (with target 60) can be removed from NBC 200 and disposed of upon reaching the end of its usable lifetime, at which point a new assembly 65 and target 60 can be inserted into NBC 200.

Figure 2C:
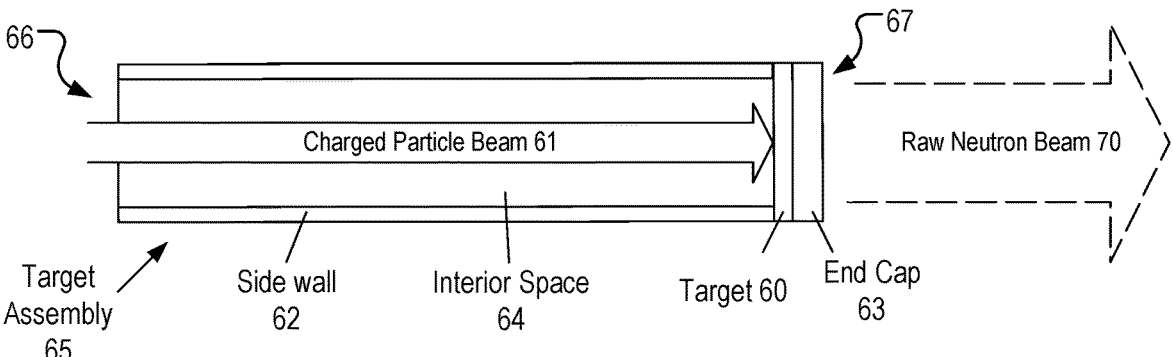
FIG. 2C shows a cross-sectional view depicting an example of an assembly for housing a neutron generating target in accordance with the present disclosure.

FIG. 2C is a cross-sectional view of an example embodiment of target assembly 65 omitting components such as valve 77, coolant channels and sensor connections for clarity. A sidewall 62 has a tubular shape and contains an interior space 64 at a vacuum or near vacuum level. Target 60 is positioned at end 67 and held in place by end cap 63. Variations of this construction are possible, such as with target 60 surrounded by sidewall 62. Charged particle beam 61 is directed through interior space 64 and scanned across target 60 by scanning magnet 74 located upstream on HEBL 50 (not shown). Neutrons produced by target 60 will be emitted at some level in virtually all directions from target 60, but the majority of the neutrons will be emitted in a disperse but generally forward directed path. This is depicted here as neutron beam 70 in raw form.

Figure 3A:
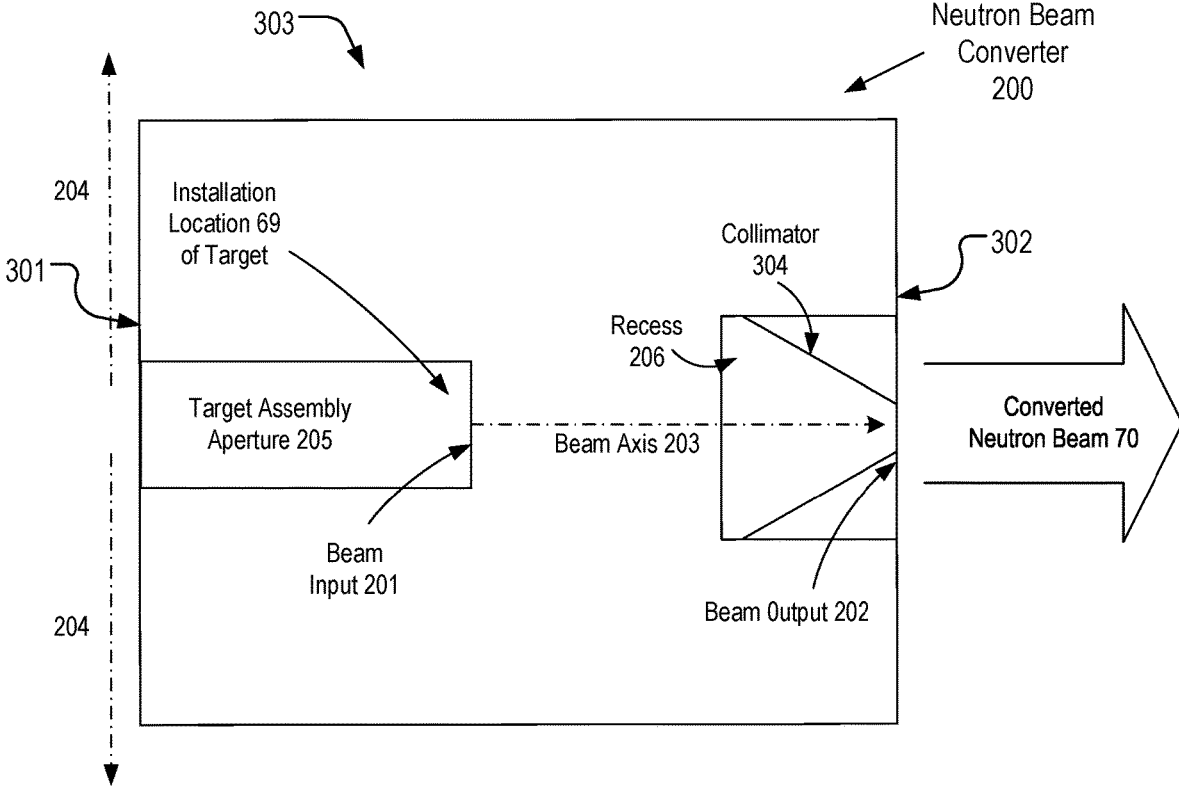
FIG. 3A shows a cross-sectional view depicting an example embodiment of a neutron beam converter in accordance with the present disclosure.

FIG. 3A is a cross-sectional view of an example embodiment of neutron beam converter (NBC) 200. NBC 200 includes a target assembly aperture 205 that is configured to receive target assembly 65 (not shown). With an assembly configuration like that described with respect to the embodiment of FIG. 2B, upon installation of assembly 65 within aperture 205, target 60 would be positioned in target installation location 69. A generally close fit can be desirable although some amount of gap will be present between assembly 65 and the surrounding walls of NBC 200 in order to permit, e.g., routing of coolant channels and periodic exchanges of assembly 65.

NBC 200 is configured to have a beam input 201 adjacent to, or in close proximity with, target installation location 69. In some embodiments, the distance between input 201 and location 69 is 10 to 60 centimeters (cm), more preferably 25 to 40 cm. NBC 200 has a beam output 202 downstream of the generated neutron flow, which is located in proximity with recess 206. An axis 203 extends from input 201 to output 202 and, in this embodiment, is located generally centrally within NBC 200. For convenience, the position of elements within NBC 200 will be referred to with respect to axis 203 and lateral directions 204, which are perpendicular to axis 203. The terms upstream and downstream are referenced with respect to charged particle beam flow into the target and subsequent neutron flow, both of which proceed in the general direction from left to right on FIG. 3A (e.g., from input 201 to output 202 along axis 203). For example, aperture 205 is axially upstream of recess 206.

Figure 3B:
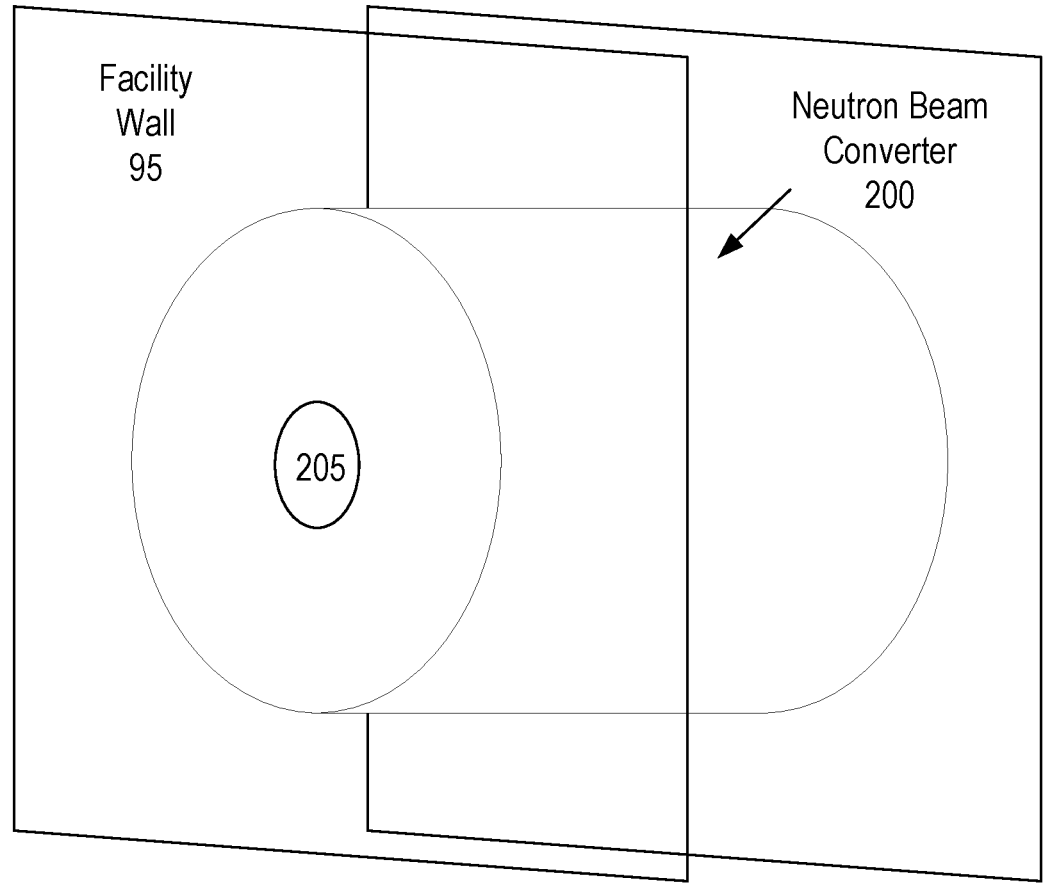
FIG. 3B shows a rear perspective view depicting an example embodiment of a neutron beam converter in accordance with the present disclosure.

NBC 200 has a rear (upstream-most) face or side 301, a front (downstream-most) face or side 302, and a lateral face or side 303. FIG. 3B depicts a perspective view of an example embodiment of NBC 200 from the upstream side. In this embodiment, structural support is provided by a concrete BNCT facility wall 95.

Due to the nature of the neutron generating reactions, the neutrons are emitted into space at many angles over a broad range of energies. Therefore, shaping and moderation of the neutron emission is required to generate an appropriate beam for treatment. To ensure an accurate dose is delivered to the patient, a real-time or near real-time neutron diagnostic is desired such that the accelerator beam can be terminated once a precise quantity of dose has been delivered to the patient. However, placing a neutron detector directly into the treatment beam subjects the detector to response changes brought on by changes in the scattering geometry that can vary from treatment to treatment. Therefore, a neutron detector in the beam is re-calibrated for every treatment. To keep the neutron detector within the line-of-sight, shielding must be placed between the detector and the patient. However, typical neutron shielding is made of hydrogenous material (e.g., polyethylene) or highly absorbing material (e.g., lithium or boron) both of which would have an adverse effect on the quality of the treatment beam. Alternatively, the neutron detector can be placed in a location that is not subject to perturbations. Thus, precise control of the accelerator can be maintained for multiple different treatments.

Neutron intensity can be measured as a function of location, angle, energy, time, or a combination thereof. For BNCT, the calibration and response of a neutron detector is specific to a unique set of conditions. In some examples, a neutron monitor is placed between the neutron beam and the patient such that any changes to the neutron delivery system, and therefore the dose to the patient, are identified in real-time. However, if any conditions or combination of conditions change, then the inferred quantity is no longer a measure of the reference conditions.

Figure 4A:
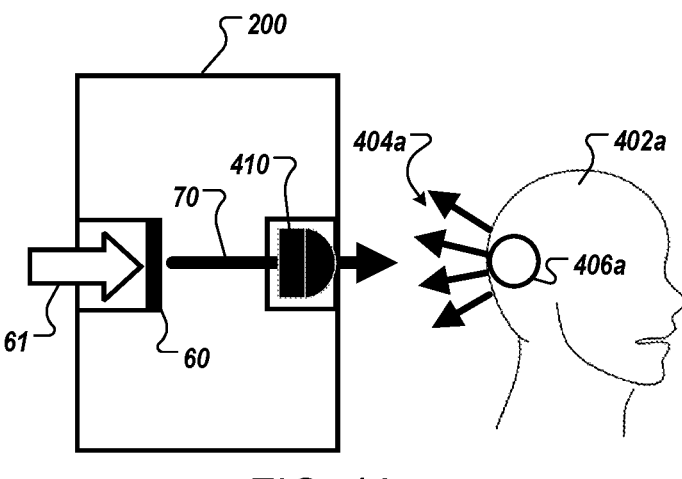
FIGS. 4A, 4B, and 4C show examples of a neutron beam propagating towards a patient with a tumor in accordance with the present disclosure.
Figure 4B:
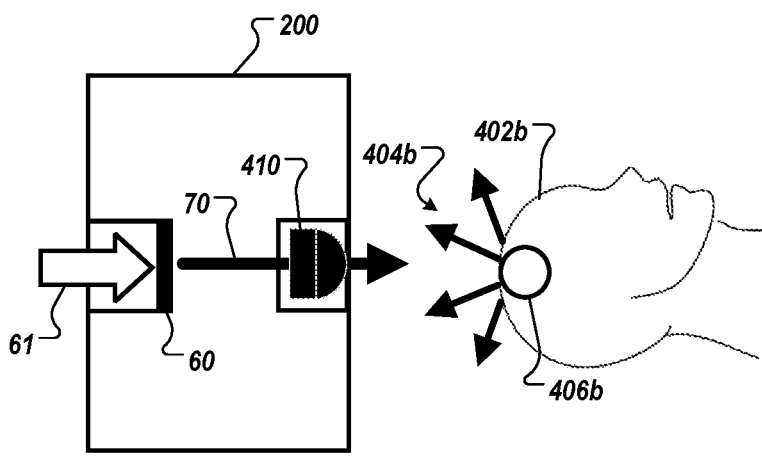
Figure 4C:
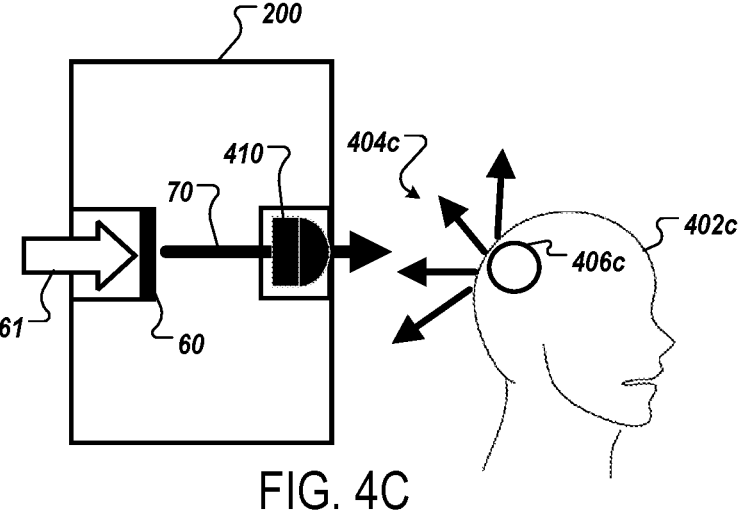

FIGS. 4A, 4B, and 4C show examples of a neutron beam propagating from an NBC 200 towards a patient with a tumor. A dosimeter, or neutron detector 410, is located between the neutron beam and the patient.

The neutron detector 410 can measure one or more of neutron fluence rate (e.g., in units of $n/cm^2s$), dose equivalent rate (e.g., in units of mrem/hr or mSv/hr), or dose equivalent (e.g., in units of mrem or mSv). The neutron detector 410 can include a neutron detection medium, a power supply, pulse shaping electronics or electrometers, an analog to digital converter, a programmable logic controller (PLC), and software.

The neutron beam propagates along an axis extending in an axial direction indicated by arrow 70. The neutron beam has a beam radius extending in a radial direction orthogonal to the axial direction. Neutrons of the neutron beam reflect off of the patient, and the reflected neutrons are detected by the neutron detector. The neutrons measured by the neutron detector includes neutrons detected from the neutron beam and neutrons reflected off the patient.

In the example of FIGS. 4A, 4B, and 4C, a neutron beam 70 travels from left to right along the axial direction. The neutron beam 70 passes through neutron detector 410 to reach a patient (e.g., patients 402*a-c*). Neutrons from the neutron beam 70 can be considered primary neutrons. The neutron beam 70 is targeted at a location of tumors 406*a-c* of patients 402*a-c*. The orientations of the patients 402*a-c* relative to the neutron beam 70 affect the reflected neutrons incident on the neutron detector 410.

Referring to FIG. 4A, the patient 402*a* has an orientation with a long dimension of the patient 402*a* being approximately normal to the beam axis. Reflected neutrons 404*a* reflect off the patient 402*a* and are detected by the neutron detector 410. The patient 402*a* is approximately centered along the beam axis. Therefore, the reflected neutrons 404*a* are detected by the neutron detector 410 approximately symmetrically.

Referring to FIG. 4B, the patient 402*b* is has an orientation with a long dimension of the patient 402*b* being approximately parallel with the beam axis. Reflected neutrons 404*b* reflect off the patient 402*b* and are detected by the neutron detector 410. The neutron detector 410 of FIG. 4B likely detects a lower reflected neutron flux compared to the neutron detector 410 of FIG. 4A due to the orientation of the patient 402*b*. The patient 402*b* is approximately centered along the beam axis. Therefore, the reflected neutrons 404*b* are detected by the neutron detector 410 approximately symmetrically.

Referring to FIG. 4C, the patient 402*c* has an orientation with a long dimension of the patient 402*c* being approximately normal to the beam axis. The patient 402*c* is off-center relative to the beam axis. Reflected neutrons 404*c* reflect off the patient 402*c* and are detected by the neutron detector 410. The neutron detector 410 of FIG. 4C likely detects a lower reflected neutron flux compared to the neutron detector 410 of FIG. 4A due to the patient 402*c* being off-center. The reflected neutrons 404*c* are detected by the neutron detector 410 asymmetrically.

The scattering of the neutrons from the patient back towards the neutron detector vary widely based on the orientation of the detector with respect to the patient location, exposed patient surface area, and composition of the patient. Neutrons that are backscattered or reflected towards the detector, on average, will have less kinetic energy, E, than the incident neutrons. Since the probability of detection is proportional to $1/\sqrt{E}$, the neutron detector will have a higher detection efficiency for reflected neutrons compared to primary incident neutrons.

Thus, neutron reflection off of a patient can result in an increase to the measured signal. The increase in the measured signal can result in an underestimation of the true dose the patient has received if the neutron detector is relied upon for dose monitoring. Therefore, to accurately monitor patient dose, the neutron detector should be calibrated for each treatment plan, shielded from reflected neutrons, placed in a location where the response does not vary by treatment plan, or any combination thereof.

Beam symmetry can be inferred with a neutron measurement using two or more independent detectors that correspond to a discreet spatial location. For a uniform incident beam, it is reasonable to expect that two or more neutron detectors would provide identical measurements. However, if the neutron reflection from a patient is not isotropic or uniform then this can introduce an artificial asymmetry in the measurement from an otherwise symmetric neutron field. This is analogous to the neutron beam depicted in FIG. 4C. Therefore, to infer neutron symmetry, a symmetry detector must either be calibrated for each treatment plan, shielded from the reflected neutrons, placed in a location where the response does not vary by treatment plan, implement a real-time or near real-time correction to account for the perturbations, or any combination thereof.

Various neutron detection techniques and detector configurations can be utilized to monitor the treatment beam. These include organic scintillators (e.g., hydrocarbons), doped scintillators (e.g., lithium or boron glass), gas multiplication detectors, ionization chambers, Geiger-Mueller tubes, and solid-state detectors (e.g., diamond or Si). Any type of neutron detector can be affected by response changes (e.g., neutron flux measurement changes) caused by neutron reflection without significant modification.

Figure 5A:
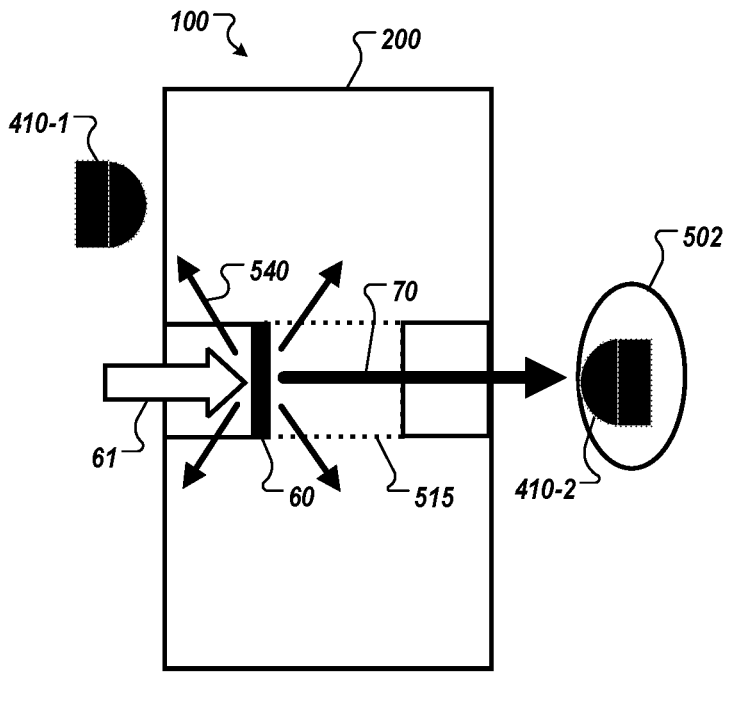
FIG. 5A shows an example embodiment of a neutron beam system configured for calibration of a neutron monitoring dosimeter in accordance with the present disclosure.
Figure 5B:
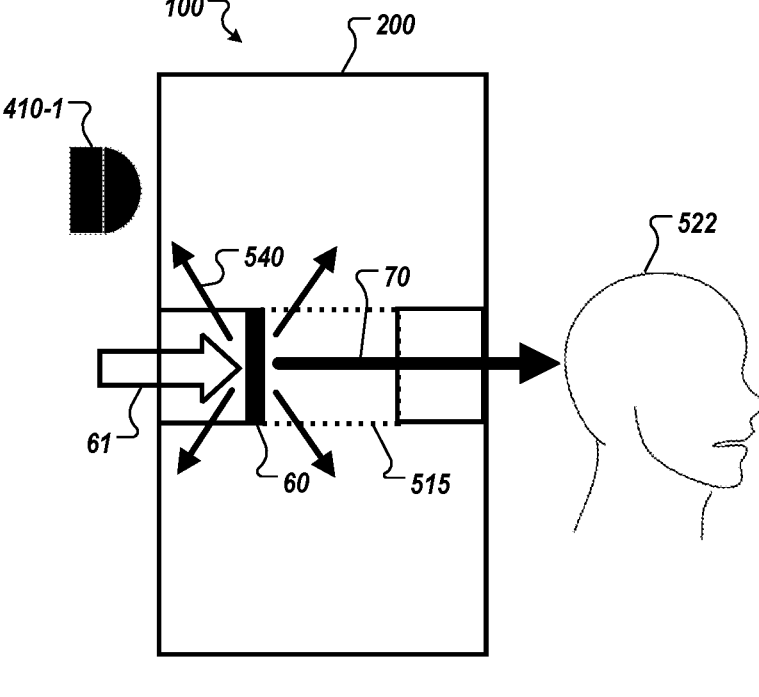
FIG. 5B shows an example embodiment of a neutron beam system configured for monitoring patient treatment using a calibrated neutron monitoring dosimeter in accordance with the present disclosure.

FIG. 5A shows an example embodiment of a portion of neutron beam system 100 configured for calibration of a neutron monitoring dosimeter. FIG. 5B shows an example embodiment of a portion of system 100 configured for monitoring patient treatment using a calibrated neutron monitoring dosimeter.

Referring to FIG. 5A, reference condition measurements can be obtained by an out-of-beam monitoring dosimeter, e.g., monitoring dosimeter 410-1, and an in-beam reference dosimeter, e.g., reference dosimeter 410-2. The monitoring dosimeter 410-1 and the reference dosimeter 410-2 can have the same or different structural configurations. In general, a substantial amount of neutrons emitted from neutron-generating target 60 propagate towards an object 502 in a neutron beam 70, though some neutrons can propagate away from the target 60 in all directions. Measurements from the monitoring dosimeter 410-1, located out of the neutron beam 70, can be used to infer conditions within the neutron beam 70.

During operation of the system 100, a charged particle beam 61 is incident on a neutron-generating target 60. In response to the incident charged particle beam 61, the target 60 emits neutrons. Due to beam shaping by the NBC 200, a subset of neutrons emitted by the target 60 propagate in a neutron beam 70. The neutron beam 70 propagates along an axial direction, e.g., left to right in FIG. 5A. The neutron beam 70 has a beam radius extending orthogonally to the axial direction.

The neutron beam 70 travels through a central region 515 of the NBC 200 and propagates along an axial direction, e.g., left to right in FIGS. 5A and 5B. Some neutrons emitted by the target 60 propagate outside of the neutron beam 70. For example, a portion of the neutrons emitted by the target 60 travel in a direction 540 towards the monitoring dosimeter 410-1.

The monitoring dosimeter 410-1 is positioned offset from the beam axis such that it is outside of (e.g., above, below, or to the side of) the neutron beam. Thus, a distance in the radial direction between the monitoring dosimeter 410-1 and the beam axis is equal to or greater than the beam radius. In some examples, the monitoring dosimeter 410-1 can be positioned outside of and behind the NBC 200, such that the NBC 200 is positioned between the monitoring dosimeter 410-1 and the object 502 in the axial direction (e.g., in a room adjacent to the treatment room). In some examples, the target 60 is positioned between the monitoring dosimeter 410-1 and the object 502 in the axial direction.

The NBC 200 provides shielding that reduces the amount of reflected neutrons detected by the out-of-beam monitoring dosimeter 410-1. Thus, the monitoring dosimeter 410-1 is less susceptible to neutron scattering and reflection off of the object 502, compared to a dosimeter that is located within the NBC 200, and compared to a dosimeter that is located between the NBC 200 and the object 502.

In some examples, the object 502 can be a surrogate for a patient. For example, the object 502 can have similar characteristics to a human or animal patient, such as the size, shape, density, and material composition of the object 502. The object 502 is formed at least partially from material that reflects neutrons. During a calibration process, the reference dosimeter 410-2 can be placed at a location on or in the object 502, e.g., at a simulated location of a tumor. The reference dosimeter 410-2 measures neutron flux received at that location. The neutron flux can be measured, for example, in units of counts per second.

System sensors can be configured to measure incident energy from the charged particle beam 61. For example, the charged particle beam 61 can be a proton beam, and the sensors can measure proton current incident on the target 60. The proton current can be measured, for example, in units of Coulombs per second. The measurement of charged particle beam energy provides a way to monitor the stability of the accelerator (e.g., accelerator 40) upstream of the target 60.

During a calibration process using the system 100, a set of reference conditions can be established. Reference conditions can include, for example, charged particle beam energy, location of the reference dosimeter 410-2, electronic parameters of the reference dosimeter 410-2, and/or treatment geometry. Treatment geometry can include characteristics of the object 502 including composition, mass, size, and/or dimensions of the object 502. The treatment geometry can also include the orientation of the object 502 and the distance of the object 502 from the NBC 200.

The reference dosimeter 410-2 can be positioned at an axial location between the target 60 and the location of the object 502. In some examples, the reference dosimeter 410-2 is placed on the object 502. Neutron flux in units of $n/(cm^2 s)$ measured by the reference dosimeter 410-2 represents neutron flux incident on the object 502.

To calibrate the monitoring dosimeter 410-1, a series of dosimetry measurements can be taken by the reference dosimeter 410-2 and by the monitoring dosimeter 410-1 simultaneously or concurrently at a set of conditions. Simultaneous measurements can be measurements that are taken within a range of time delays. For example, simultaneous measurements can be measurements that are obtained within a time delay of one second or less (e.g., 0.5 seconds or less, 0.1 seconds or less, 0.05 seconds or less). The measurements taken by the reference dosimeter 410-2 can be correlated to the measurements taken by the monitoring dosimeter 410-1. Thus, the monitoring dosimeter 410-1 can be calibrated for the set of conditions.

The set of reference conditions can also be simulated using a simulation model such as a Monte Carlo radiative transport model. Correction factors can be determined by comparing results of the simulation at the set of conditions to the measurements taken by the monitoring dosimeter 410-1 and the reference dosimeter 410-2 at the set of conditions.

In general, a correction factor, F, for the set of reference conditions can be used to correlate the predicted and measured results using a ratio, where D corresponds to a measurable quantity and D' refers to a calculated value. For example, the calculated value can be a value calculated using a simulation model. Equation 1 provides a definition for a correction factor.

$$F_{correction} = \frac{D_{measured}}{D'_{predicted}}$$   Equation 1

A constant C can be introduced to relate a reference dose (e.g., dose measured by the reference dosimeter 410-2, $D_{REF}$) and the dose measured by the monitoring dosimeter 410-1 ($D_{MD}$). Equation 2 provides a relationship between $D_{REF}$ and $D_{MD}$.

$$D_{MD} = CD_{REF}$$   Equation 2

An example of a correction factor for the monitoring dosimeter 410-1 is provided by Equation 3. An example of a correction factor for the reference dosimeter 410-2 is provided by Equation 4.

$$F_{MD} = \frac{D_{MD}}{D'_{MD}}$$   Equation 3

$$F_{REF} = \frac{D_{REF}}{D'_{REF}}$$   Equation 4

In Equation 3, $D'_{MD}$ represents the calculated dose at the location of the monitoring dosimeter 410-1, and $D_{MD}$ represents the actual dose measured by the monitoring dosimeter 410-1. Similarly, in Equation 4, $D'_{REF}$ represents the calculated dose at the location of the reference dosimeter 410-2, and $D_{REF}$ represents the actual dose measured by the reference dosimeter 410-2.

Equation 5, below, provides a relationship between: a ratio of actual dose measured by the monitoring dosimeter 410-1 and the dose at the location of the reference dosimeter 410-2 during calibration, and a ratio between calculated dose at the location of the monitoring dosimeter 410-1 and calculated dose at the location of the reference dosimeter 410-2.

$$C = \frac{D_{MD}}{D_{REF}} = \frac{F_{MD}D'_{MD}}{F_{REF}D'_{REF}}$$   Equation 5

Solving Equation 5 for $D_{MD}$, Equation 6 shows a relationship between dose measured by the monitoring dosimeter 410-1 and the dose at the location of the reference dosimeter 410-2.

$$D_{MD} = \frac{F_{MD}D'_{MD}}{F_{REF}D'_{REF}}D_{REF}$$   Equation 6

Referring to FIG. 5B, the dose measured by the monitoring dosimeter 410-1 monitors the dose over time to determine a total dose provided to a patient 522. The system 100, illustrated in FIG. 5B, does not include a reference dosimeter. Neutron flux at the patient 522 can be inferred using the dose measured by the monitoring dosimeter 410-1 and the relationships determined using the calibration process described with reference to FIG. 5A.

In a treatment scenario such as illustrated in FIG. 5B, $D_{REF}$ can represent the dose at the location of the patient 522, e.g., the dose that would be measured by a reference dosimeter if a reference dosimeter was positioned at the patient location during treatment. The variable $D_{REF}$ can therefore be substituted with a desired dose $D_{DES}$, e.g., the dose prescribed by the treatment plan to be provided at the location of the patient 522. Equation 7 shows the substitution of $D_{REF}$ with $D_{DES}$ into Equation 6.

$$D_{MD} = \frac{F_{MD}D'_{MD}}{F_{REF}D'_{REF}}D_{DES}$$   Equation 7

Equation 7 provides the $D_{MD}$ that is predicted to be measured by the monitoring dosimeter 410-1 for a corresponding desired dose $D_{DES}$. Using Equation 7, a target dose at the monitoring dosimeter ($D_{MD}$) can be determined based on the desired dose at the patient ($D_{DES}$).

In some examples, the dose measured by the monitoring dosimeter 410-1 can be used to monitor beam fluctuations over time. In some examples, the dose measured by the monitoring dosimeter 410-1 can be used to determine when to terminate the accelerator beam, whether to increase or decrease a length of time of treatment to ensure the proper dose is administered, whether to increase or decrease the magnitude of the charged particle beam, whether to increase or decrease the rate of generation of neutrons by the system, as a safeguard to ensure the expected amount of neutrons is being generated, to generate an indicator (e.g., an audible and/or visual cue) to an operator that neutron radiation currently is present, and the like. For example, a control system for the accelerator 40 receives the monitoring dosimeter 410-1 measurement as input, and can determine a total dose provided to the patient over time. Once the desired dose has been reached, as specified by the treatment plan, the control system can control the accelerator 40 to cease propagation of the charged particle beam 61. Operations of control systems are described in greater detail with reference to FIG. 7.

The calibration process illustrated in FIG. 5B can be performed more than once. For example, the calibration process can be performed routinely or occasionally (e.g., before each patient treatment, once each day that the system is operated, once a week, once a month, and/or after a predetermined time of usage of the system or target has expired, whenever a new target is installed) or otherwise when needed. The correction factors can change over time due, for example, due to changes in characteristics of the target 60 due to aging.

The use of a monitoring dosimeter 410-1 outside of the neutron beam provides an advantage of having a standardized measurement that does not require re-calibration of the device for every treatment, and therefore increases the accuracy of dose measurement. In addition, treatment facility throughput can be improved due to the reduced time needed to perform a separate calibration for each treatment plan.

This use of a monitoring dosimeter 410-1 outside of the neutron beam allows for a direct relationship to be established between the desired treatment plan dose and a neutron measurement. The neutron dosimetry provides methods to monitor real-time fluctuations in the neutron rate and as methods to control the precise delivery of a specific quantity of dose.

Figure 6A:
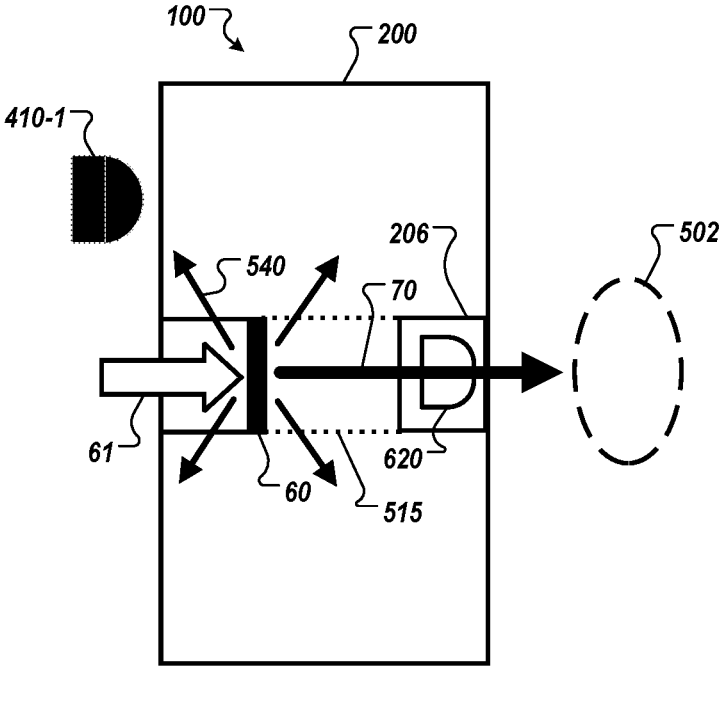
FIG. 6A shows an example embodiment of a neutron beam system configured for calibration of a symmetry monitoring system in accordance with the present disclosure.
Figure 6C:
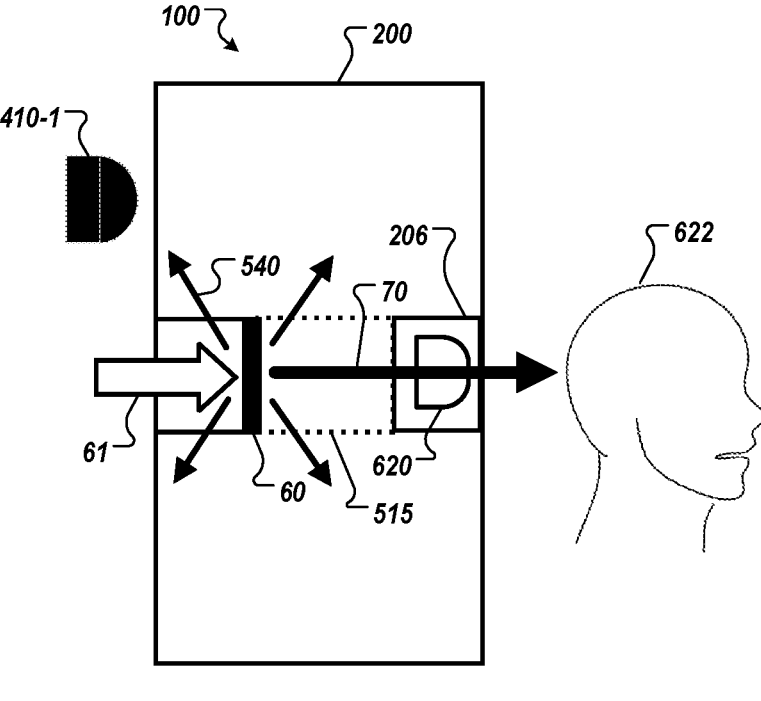
FIG. 6C shows an example embodiment of a neutron beam system configured for monitoring patient treatment using a calibrated symmetry monitoring system.

Neutron monitoring for BNCT can be performed in terms of dose delivered to the patient over an area where the neutron beam is uniform and symmetric. A symmetry measurement can be performed when the neutron monitors are placed between the source of the neutron beam and the patient such that any changes to the neutron symmetry, and therefore the dose to the patient, are identified in real-time. FIG. 6A shows an example embodiment of system 100 configured for calibration of a symmetry detector. FIG. 6C shows an example embodiment of system 100 configured for monitoring patient treatment using a calibrated symmetry detector.

Referring to FIG. 6A, reference condition measurements can be obtained by an out-of-beam monitoring dosimeter, e.g., monitoring dosimeter 410-1, and an in-beam symmetry monitoring system, e.g., symmetry detector 620. Reference measurements to be used for calibration can optionally be obtained with object 502 positioned across or on the axis of the neutron beam 70. Reference measurements to be used for calibration can optionally be obtained without any object positioned across or on the axis of the neutron beam 70.

As with the embodiment of FIGS. 5A and 5B, neutron beam 70 travels through a central region 515 of the NBC 200 and propagates along an axial direction, e.g., left to right in FIGS. 6A and 6C. The monitoring dosimeter 410-1 can again be positioned offset from and outside of the neutron beam, e.g., with a distance in the radial direction between the monitoring dosimeter 410-1 and the beam axis being equal to or greater than the beam radius.

In some examples, as shown in FIG. 6A, the monitoring dosimeter 410-1 can be positioned outside of the NBC 200, such that the NBC 200 is positioned between the monitoring dosimeter 410-1 and the object 502 in the axial direction. With the NBC 200 positioned between the monitoring dosimeter 410-1 and the object 502, the monitoring dosimeter 410-1 is less susceptible to neutron scattering and reflection off of the object 502. This improves consistency from treatment to treatment, improving the accuracy of dose measurement and reducing or eliminating the need for calibration of the monitoring dosimeter 410-1 for individual treatments.

The monitoring dosimeter 410-1 in FIG. 6A is shown as being positioned outside of and behind the NBC 200, such that the NBC 200 is between the monitoring dosimeter 410-1 and the object 502 in the axial direction. Other configurations are possible. In some examples, the monitoring dosimeter 410-1 can be positioned outside of and above the NBC 200, outside of and below the NBC 200, or outside of and to the side of the NBC 200. In some examples, the monitoring dosimeter 410-1 can be positioned outside of and in front of the NBC 200, such that the monitoring dosimeter 410-1 is located between the NBC 200 and the object 502 in the axial direction.

In some examples, the monitoring dosimeter 410-1 is located within the NBC 200. For example, the monitoring dosimeter 410-1 can be located within the NBC 200 and above the neutron beam, below the neutron beam, or to the side of the neutron beam. The monitoring dosimeter 410-1 can be located within the NBC 200 behind the target 60 (e.g., with the target 60 between the monitoring dosimeter 410-1 and the object 502 in the axial direction), aligned with the target 60 (e.g., with the target 60 and the monitoring dosimeter 410-1 being equidistant from the object 502 in the axial direction), or in front of the target 60 (e.g., with the monitoring dosimeter 410-1 between the target 60 and the object 502 in the axial direction).

With the monitoring dosimeter 410-1 being positioned within the NBC 200, the monitoring dosimeter 410-1 may be more susceptible to neutron scattering and reflection off of the object 502 compared to the monitoring dosimeter 410-1 positioned behind the NBC 200. With the monitoring dosimeter 410-1 being positioned within the NBC 200, the monitoring dosimeter 410-1 may be less susceptible to neutron scattering and reflection off of the object 502 compared to the monitoring dosimeter 410-1 being positioned in front of the NBC 200.

The symmetry detector 620 is configured to monitor, or facilitate monitoring, of the symmetry of the neutron beam 70. The symmetry detector 620 is positioned such that it intersects the axis of the neutron beam 70. Due to the position of the symmetry detector 620, the symmetry detector 620 is susceptible to interference from neutrons reflected off of a patient. However, placement of the symmetry detector 620 inside the beam radius, in the central region 515, is more accurate than placement of a symmetry detector 620 outside of the beam radius, since a symmetry detector located outside of the beam radius might not be able to detect a local change to the symmetry, e.g., between the beam and patient. For example, a local change to the symmetry might not be measurable outside of the beam radius due to smoothing of the beam due to geometric effects. In some examples, multiple scattering events can make the local in-beam asymmetry appear symmetric outside of the beam.

Figure 6B:
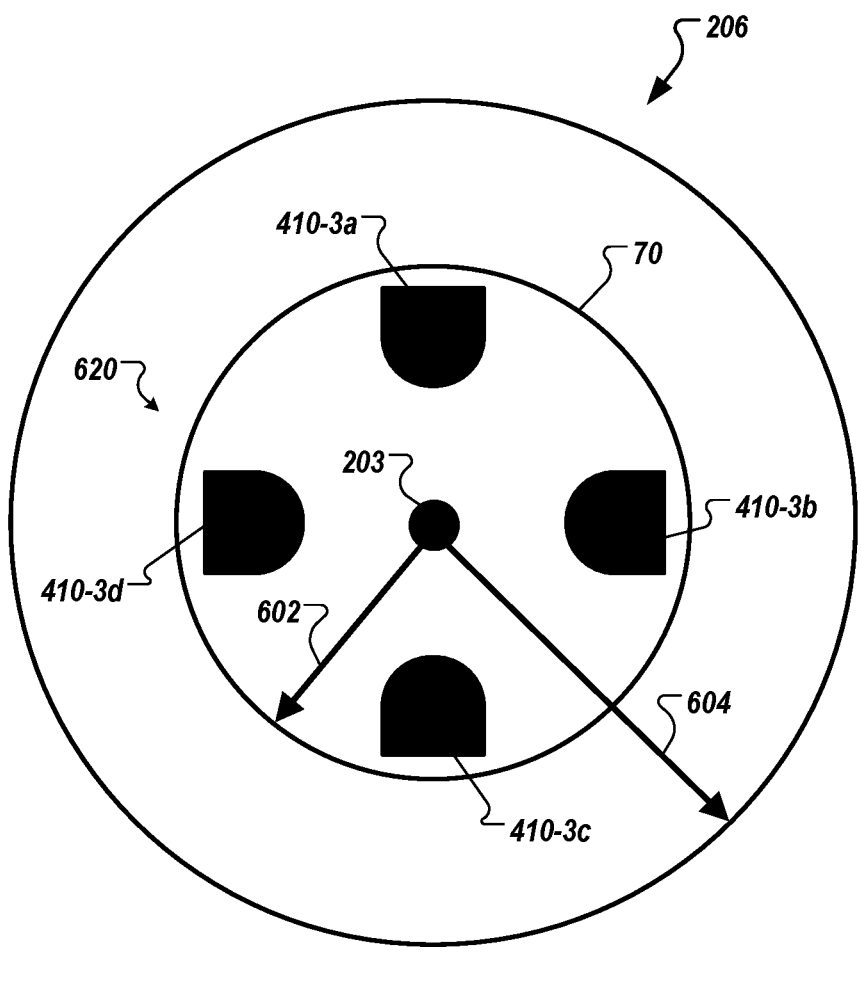
FIG. 6B shows a cross-sectional view of an example neutron beam in accordance with the present disclosure.

FIG. 6B shows a cross-sectional view of an example neutron beam 70 passing through recess 206. The symmetry detector 620 can include two or more individual dosimeters 410-3*a*, 410-3*b*, 410-3*c*, 410-3*d* (collectively referred to as "dosimeters 410-3"). In some examples, the symmetry detector 620 can include a single array of dosimeters. In the example of FIG. 6B, the four individual dosimeters 410-3 of the symmetry detector 620 are each located at a pole around the beam axis 203. The dosimeters 410-3 are arranged at different azimuthal positions around the beam axis 203 of the neutron beam 70. In some examples, the dosimeters 410-3 are equidistant from the neutron-generating target 60 in the axial direction. In some examples, the dosimeters 410-3 of the symmetry detector 620 are positioned at a fixed distance from the target 60, with a fixed amount of material between the target 60 and the symmetry detector 620.

In some examples, the dosimeters 410-3 are equidistant from the beam axis in the radial direction. The dosimeters of the symmetry detector 620 can be placed at or near the periphery 606 of the neutron beam. For example, a distance between each dosimeter 410-3 and the beam axis 203 can be equal to or less than the beam radius 602. In some examples, a sensitivity analysis, e.g., using Monte Carlo neutron simulation, can be performed to determine optimal radial and/or axial positions of the dosimeters 410-3.

In some examples, the dosimeters 410-3 can be positioned in a beam exit cavity of the NBC 200. For example, the dosimeters 410-3 can be positioned in the recess 206 of the NBC 200, with the distance between each dosimeter 410-3 and the beam axis 203 being less than the radius 604 of the recess 206. In some examples, the distance between each dosimeter 410-3 and the beam axis 203 can be approximately half of the radius 604 of the recess 206.

Using the individual dosimeters 410-3, the symmetry detector 620 measures neutron flux received at multiple edges of the beam. The neutron flux can be measured, for example, in units of counts per second.

The NBC 200 controls the width and shape of the neutron beam 70. Generally, the desired shape of the neutron beam 70 is symmetrical, with a planar neutron flux, with the normal vector of the plane along the beam axis. In a planar neutron flux, each dosimeter 410-3 of the symmetry detector 620 detects a same neutron flux due to uniform flux distribution over the beam width.

In a scenario where no object 502 is present, the dosimeters 410-3 of the symmetry detector 620 should each detect the same or substantially the same neutron flux when the neutron beam is symmetrical. When an object 502 is in the path of the neutron beam 70, some neutrons will reflect off of the object 502 and be detected by the symmetry detector 620. Thus, the dosimeters 410-3 of the symmetry detector 620 may detect significantly different neutron fluxes from each other (e.g., in some embodiments differences greater than about 1%, or in other embodiments differences greater than about 3%), when the neutron beam is symmetrical and the object 502 is in the path of the neutron beam 70. The symmetry detector 620 can be calibrated for different object and patient geometries, in order to be able to detect symmetry disturbances when accounting for reflected neutrons.

The system 100 can be used to calibrate the symmetry detector 620 for expected perturbations by correlating a set of reference conditions without any object present to a set of conditions with an object present. The calibrated symmetry detector 620 can then be used during patient treatment to detect unexpected changes to neutron flux symmetry. For example, neutron flux symmetry can change unexpectedly due to an event such as movement of the NBC 200, movement of the patient, movement of a patient support structure, or any combination of these. Movement of the patient can include a change in orientation or distance of the patient, for example due to a tilting of the patient's head, the patient's arm falling off of an armrest, etc.

In some examples, symmetry calibration can be performed for each dosimeter of the symmetry detector 620. For simplicity, the following discussion of symmetry calibration refers to a single dosimeter of the symmetry detector 620.

To calibrate the symmetry detector 620, reference measurements to be used for calibration can be obtained in a "bare" condition without any object positioned along the neutron beam 70 and in a "reference" condition with an object 502 positioned along the neutron beam 70. In the bare condition, measurements can be obtained with the accelerator 40 set to nominal parameters for beam current, energy, spot size, and duration.

In the reference condition, the same accelerator parameters are used in addition to a nominal treatment geometry including a surrogate patient, e.g., object 502 being positioned in the path of the neutron beam 70. The object 502 is an object of known composition, mass, dimensions at a specified distance from the NBC 200.

The treatment geometry can include parameters of collimators 304 located between the target 60 and the patient. In some examples, a collimator 304 or series of collimators 304 (not shown) is located downstream from the symmetry detector 620. The collimator 304 can shield secondary radiation and resize the field of the neutron beam to be appropriate for the treatment. the collimator 304 can shape the beam field and can reflect backward-moving neutrons reflecting from the patient. The collimator 304 can be made from shielding material such as lead, graphite, and borated polyethylene. The collimator 304 can limit divergence of the neutron beam, reduce undesired irradiation, and focus neutrons to the patient position.

In some examples, a collimator has a fixed length and a variable inner diameter and a fixed outer diameter, such that an outer cone angle is fixed and an inner cone angle is variable. The collimator 304 affects the beam diameter at the point where the beam reaches the patient. While the primary neutron flux detected at the symmetry detector 620 from the neutron beam 70 is not affected by changes in collimator 304 size, the detector response due to neutron reflection will vary with changes in collimator 304 size. For each collimator 304, a reference geometry and correlation can be established and corrected for every treatment. The size of the collimator 304, the shape of the collimator 304, or both, can be selected based on the treatment plan for the patient.

In some examples, the positioning of collimators 304 is dynamic. A controller and actuator can be provided to adjust a position of a collimator 304 relative to the beam axis 203. In some examples, the actuator, when instructed by the controller, can place a collimator 304 along the beam axis 203 and remove the collimator 304 from along the beam axis 203. In some examples, the actuator can replace one collimator 304 with another collimator. Thus, collimators 304 of various shapes and sizes can be swapped and/or repositioned to satisfy requirements of various treatment plans.

A series of dosimetry measurements are taken with the symmetry detector 620 in bare and reference conditions and correlated to the monitoring dosimeter 410-1 response as an absolute calibration. The monitoring dosimeter 410-1 located outside of the neutron beam 70 is protected from changes in the reference geometry. Therefore, the monitoring dosimeter 410-1 serves as an absolute calibration of the target 60 and the NBC 200.

In some examples, an expected response of the symmetry detector 620 can be derived through Monte Carlo simulation of the beam's response to, and reflection from, a patient. Predicted relative dose amounts at each dosimeter 410-3 of the symmetry detector 620 can be determined from the simulation. Then, during treatment, the responses of each dosimeter 410-3 can be monitored, and the relative measurements can be compared to the expected values determined using the simulation. The cause of an unfavorable comparison can be determined and then corrected with active feedback, beam stoppage, or both. Examples of deviations from expected values and resulting actions are described in greater detail below.

In some examples, an expected response of the symmetry detector 620 can be determined empirically. The neutron beam 70 can be emitted under conditions at which symmetrical reflection is expected. For example, the neutron beam 70 can be emitted at a uniform, symmetrical object, or at no object. Relative and/or absolute neutron detection measurements can be obtained from each dosimeter 410-3 of the symmetry detector 620. The neutron detection measurements from the individual dosimeters under symmetrical conditions can be used to calibrate the dosimeters to generate the same output under those conditions.

In an example, the symmetry detector 620 includes four dosimeters "410-3a," "410-3b," "410-3c," "410-3d," with respective measurement outputs "$D_a$," "$D_b$," "$D_C$," and "$D_d$." A particular dosimeter can be assigned as a baseline dosimeter. For example, the dosimeter A having the measurement output $D_a$ can be assigned as a baseline dosimeter. Neutron detection measurements under a reference symmetric condition can be obtained from all four dosimeters. The control system can determine ratios between the measurement obtained from each dosimeter compared to the measurement obtained from the baseline dosimeter, e.g., the ratios $D_b/D_a$, $D_c/D_a$, and $D_d/D_a$. The ratios can be stored as calibration data for the symmetry detector 620. To calibrate the symmetry detector 620, the measured responses of each dosimeter can be adjusted based on the stored ratios. Thus, the responses from the four dosimeters should match each other, within a specified tolerance for the symmetric reference condition.

With the dosimeters 410-3 calibrated to output matching responses for a symmetric reference condition, a threshold error, or error parameter $\zeta$, can be introduced to monitor deviations between individual dosimeters 410-3. In Equation 8 below, the error parameter $\zeta$ can be a user-defined error parameter. Variable $D_n$ is the dose measured by dosimeter 410-3n, where n=a, b, c, or d. Variable $D_m$ is the dose measured by dosimeter 410-3m, where m=a, b, c, or d and n≠m. If the condition specified by Equation 8 is not satisfied for one or more pairs of dosimeters, then the control system can determine that at least one parameter in the treatment deviates from the expected conditions.

$$\zeta \geq \frac{|D_n(t) - D_m(t)|}{D_n} \qquad \text{Equation 8}$$

In response to determining that the treatment conditions are deviating from the expected conditions, the control system can perform one or more actions. The actions can include, for example, stopping treatment by ceasing operations of the accelerator 40. In some examples, the action can include activating an alert or alarm to signal to an operator that an anomaly exists. In some examples, the action can include adjusting one or more settings of the accelerator 40, of the NBC 200, or both. For example, in response to detecting an error in symmetry of the neutron beam, as measured by one or more of the dosimeters 410-3 of the symmetry detector 620, the control system can adjust the NBC 200 in order to reduce or correct the error.

In some examples, correction factors can be determined by simulating bare and reference conditions using a simulation model, e.g., a Monte Carlo radiative transport code. Correction factors can be determined by comparing results of the simulation at a set of conditions to the measurements taken by the monitoring dosimeter 410-1 and the symmetry detector 620 at the same set of conditions.

In general, a correction factor, F, for the reference conditions can be used to correlate the predicted and measured results using a ratio, where D corresponds to a measurable quantity and D' refers to a calculated value. For example, the calculated value can be a value calculated using a simulation model. Equation 1 above provides a definition for a correction factor.

A constant C can be used to relate a reference dose (e.g., dose measured by a dosimeter of the symmetry detector 620, $D_{SYM}$) and the dose measured by the monitoring dosimeter 410-1 ($D_{MD}$). Equation 9 provides a relationship between $D_{SYM}$ and $D_{MD}$.

$$D_{MD} = CD_{SYM} \qquad \text{Equation 9}$$

A correction factor for the monitoring dosimeter 410-1 is provided by Equation 10. A correction factor for the symmetry detector 620 is provided by Equation 11.

$$F_{MD} = \frac{D_{MD}}{D'_{MD}} \qquad \text{Equation 10}$$

$$F_{SYM} = \frac{D_{SYM}}{D'_{SYM}} \qquad \text{Equation 11}$$

In Equation 10, $D'_{MD}$ represents the calculated dose at the location of the monitoring dosimeter 410-1, and $D_{MD}$ represents the actual dose measured by the monitoring dosimeter 410-1. Similarly, in Equation 11, $D'_{SYM}$ represents the calculated dose at the location of a dosimeter of the symmetry detector 620, and $D_{SYM}$ represents the actual dose measured by a dosimeter of the symmetry detector 620.

Referring to FIG. 6C, the dose measured by the symmetry detector 620 can be used to monitor neutron symmetry over time while treating a patient 622. Solving for C and combining equations provides the dose that is predicted to be measured by a dosimeter of the symmetry detector 620 for a corresponding measured dose $D_{MD}$. The measured dose $D_{MD}$ can be a dose that is predicted to be measured by the monitoring dosimeter 410-1 when the patient 622 is provided a dose prescribed by the treatment plan.

Equation 12, below, provides a relationship between: a ratio of actual dose measured by the monitoring dosimeter 410-1 and the dose at the location of a dosimeter of the symmetry detector 620, and a ratio between calculated dose at the location of the monitoring dosimeter 410-1 and calculated dose at the location of the dosimeter of the symmetry detector 620. Equation 12 shows a relationship between dose measured by the monitoring dosimeter 410-1 and the dose at the location of the dosimeter of the symmetry detector 620.

$$C = \frac{D_{MD}}{D_{SYM}} = \frac{F_{MD}D'_{MD}}{F_{SYM}D'_{SYM}} \qquad \text{Equation 12}$$

$$D_{MD} = \frac{F_{MD}D'_{MD}}{F_{SYM}D'_{SYM}}D_{SYM} \qquad \text{Equation 13}$$

Using Equation 13, the predicted dose measured by the dosimeter of the symmetry detector 620 ($D_{SYM}$) can be predicted by measuring the dose at the monitoring dosimeter ($D_{MD}$). Additionally, given a target $D_{MD}$, a target $D_{SYM}$ can be determined using Equation 13. In some examples, a target $D_{MD}$ can be determined based on the prescribed $D_{DES}$, using Equation 8. The target $D_{SYM}$ can then be determined based on the target $D_{MD}$, using Equation 13.

Predicted dosimetry measurements can be determined for each individual dosimeter 410-3 of the symmetry detector 620 under various sets of conditions. During treatment, the measurement obtained from each dosimeter 410-3 can be compared to the predicted dosimetry measurement of the dosimeter 410-3 in order to monitor treatment.

Once a predictive capability has been established for the symmetry detector 620, a threshold error, or error parameter $\zeta$, can be introduced to monitor perturbations in the treatment plan. In Equation 14 below, the error parameter $\zeta$ can be a user-defined error parameter, $D_{SYM}$ is the expected dose measured by a dosimeter of the symmetry detector 620, and $D_{ACTUAL}$ is the uncorrected experimental dose from the same dosimeter of the symmetry detector 620.

If the condition specified by Equation 14 is not satisfied, then the control system can determine that at least one parameter in the treatment deviates from the expected conditions.

$$\zeta \geq \frac{|D_{sym}(t) - D_{actual}(t)|}{D_{sym}(t)} \qquad \text{Equation 14}$$

In some examples, the control system can apply a coincidence logic to determine if treatment parameters are deviating from expected conditions outside of error tolerance. For example, coincidence logic can specify that if the condition specified by Equation 14 is satisfied for at least a threshold number of dosimeters of the symmetry detector 620, the treatment conditions are deviating from expected conditions outside of error tolerance. In an example, the control system can determine that conditions have deviated from expected conditions outside of error tolerance based on determining that the dosimetry measurements of two or more dosimeters 410-3 of the symmetry detector 620 satisfy the conditions of Equation 14.

The control system can determine that the error exceeds a threshold error, e.g., using Equation 14, and can perform one or more actions in response. The actions can include, for example, stopping treatment by ceasing operations of the accelerator 40. In some examples, the action can include activating an alert or alarm to signal to an operator that an anomaly exists. In some examples, the action can include adjusting one or more settings of the accelerator 40, of the NBC 200, or both. For example, in response to detecting an error in symmetry of the neutron beam, the control system can adjust the NBC 200 in order to reduce or correct the error.

Figure 7:
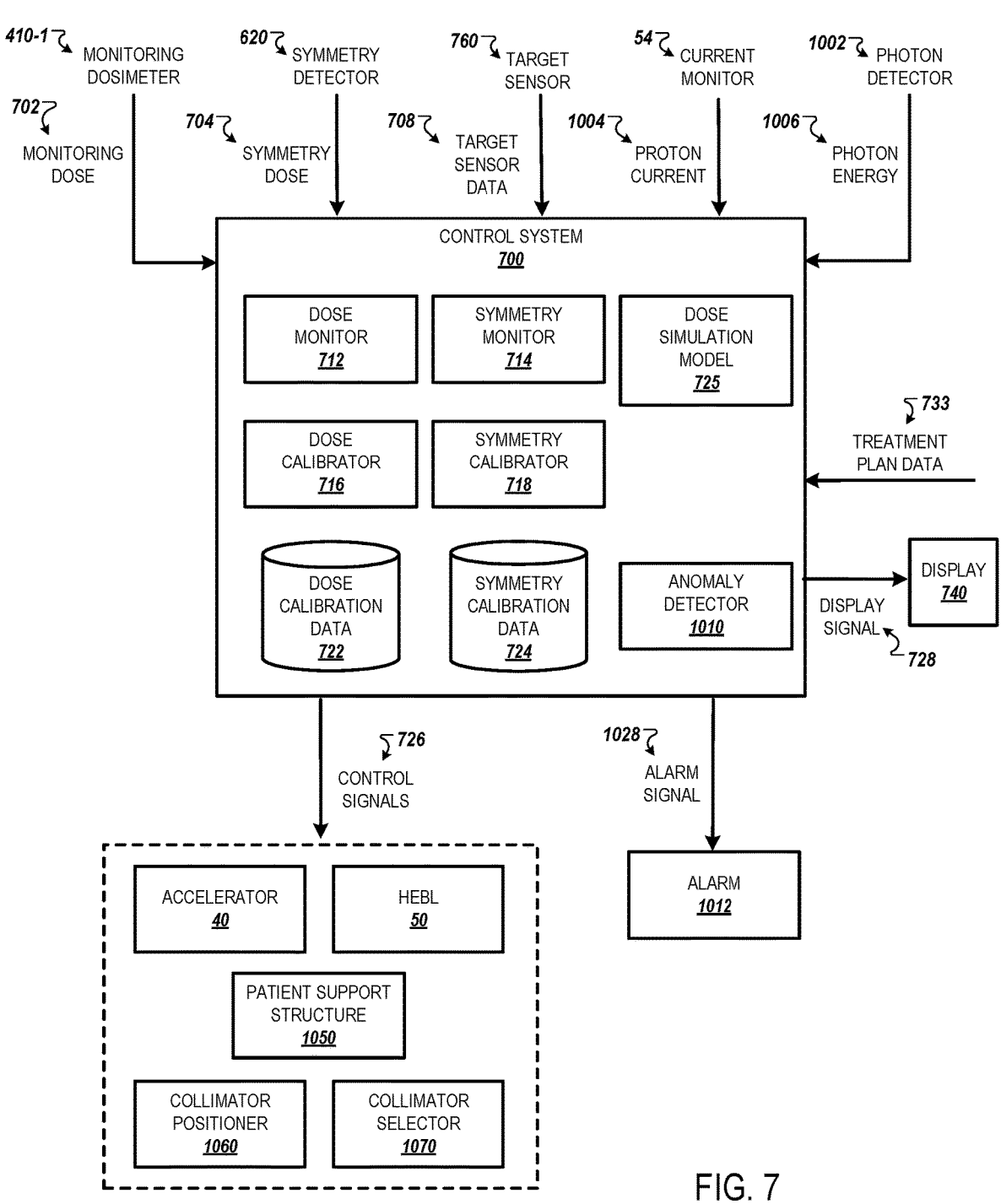
FIG. 7 shows an example embodiment of a control system configured for neutron beam monitoring and control in accordance with the present disclosure.

FIG. 7 shows an example control system 700 for neutron beam monitoring and control. The control system 700 includes a dose calibrator 716, symmetry calibrator 718, dose calibration data 722, and symmetry calibration data 724. The control system 700 includes a dose monitor 712, symmetry monitor 714, a dose simulation model 725, and an anomaly detector 1010.

In some implementations, the control system 700 includes a set of operation modules for controlling different aspects neutron beam monitoring and control. The operation modules can be provided as one or more computer executable software modules, hardware modules, or a combination thereof. For example, one or more of the operation modules can be implemented as blocks of software code with instructions that cause one or more processors of the control system 700 to execute operations described herein. In addition or alternatively, one or more of the operation modules can be implemented in electronic circuitry such as, e.g., programmable logic circuits, field programmable logic arrays (FPGA), or application specific integrated circuits (ASIC). The operation modules can include the dose calibrator 716, symmetry calibrator 718, dose monitor 712, symmetry monitor 714, and dose simulation model 725.

The control system 700 receives input from a monitoring dosimeter 410-1, a symmetry detector 620, a reference dosimeter 711, one or more target sensors 760 associated with a neutron-generating target 60, a current monitor 54, a photon detector 1002, or any combination of these. The control system 700 receives a monitoring dose 702 (or information indicative of or allowing calculation of a monitoring dose) from the monitoring dosimeter 410-1. The control system 700 receives a symmetry dose 704 (or information indicative of or allowing calculation of a symmetry dose) from the symmetry detector 620. The control system 700 receives a reference dose 706 (or information indicative of or allowing calculation of a reference dose) from the reference dosimeter 711. The control system 700 receives target sensor data 708 (e.g., information indicative of or allowing calculation of a charged particle energy incident on the target, information indicative or allowing calculation of target temperature) from system sensors associated with the target (e.g., target sensors 760). The control system 700 receives proton current data 1004 (or information indicative of or allowing calculation of a proton current) from the current monitor 54. The control system 700 receives photon energy data 1006 (or information indicative of or allowing calculation of a photon energy) from the photon detector 1002.

The dose calibrator 716 can perform dose calibration for multiple different sets of conditions. For example, dose calibration can be performed as described with reference to the system 100 of FIG. 6A. The dose calibrator 716 can determine correction factors between the monitoring dose 702 and the reference dose 706. The dose calibrator 716 can determine correction factors between the measured doses and doses calculated using the dose simulation model 725.

Dose calibration data 722 generated from the dose calibration can be stored, e.g., in a database. The dose calibration data 722 can include correlations between the monitoring dose 702 and the reference dose 706 at each of multiple sets of conditions. In some examples, the dose calibration data 722 includes correction factors $F_{MD}$, $F_{REF}$, $F_{MD}/F_{REF}$, or any of these.

The dose monitor 712 can monitor neutron dose provided to a patient during BNCT treatment. The dose monitor 712 can monitor the neutron dose based on the calibration data 722 generated from the calibration process. The dose monitor 712 can monitor the neutron dose using the monitoring dose 702 output by the monitoring dosimeter 410-1.

Inputs to the dose monitor 712 can include treatment plan data 733, dose calibration data 722, the monitoring dose 702. To monitor neutron flux incident on a patient during BNCT treatment, the dose monitor 712 obtains treatment plan data 733 indicating a set of conditions at which the neutron beam is or is to be directed towards the patient during the BNCT treatment. The treatment plan data 733 can include set of conditions for directing the neutron beam to the patient. The conditions can include, for example, a geometry (e.g., size, dimensions, distance, orientation) of the patient. The treatment plan data 733 can include a neutron dose to be delivered to the patient.

The dose monitor 712 can select, from the multiple different sets of conditions represented in the dose calibration data 722, a first set of conditions indicative of the conditions specified by the treatment plan data 733. The dose monitor 712 obtains the calibration data 722 corresponding to the selected set of conditions. In some examples, the dose monitor 712 can select a set of conditions that satisfy similarity criteria for matching the conditions specified by the treatment plan data 733. In some examples, the dose monitor 712 can select a set of conditions that most closely matches the set of conditions specified by the treatment plan data 733. In some examples, the dose monitor 712 can select a set of conditions that is more similar to the conditions specified by the treatment plan data 733 than any other set of conditions of the multiple different sets of conditions.

During treatment, the dose monitor 712 obtains data indicating the monitoring dose 702 measured by the monitoring dosimeter 410-1. The dose monitor 712 can determine, using the monitoring dose 702 and the calibration data 722, the neutron flux incident on the patient. In some examples, the dose monitor 712 can determine the neutron flux by adjusting a measured or calculated dose based on the set of conditions at which the treatment is performed. For example, the set of conditions specified by the treatment plan data 733 can be different from the selected set of conditions represented in the dose calibration data 722. The dose monitor 712 can adjust and/or weight the dose measurements, e.g., as determined using monitoring dose 702, to account for the difference and to align with the set of conditions at which the treatment is being performed. In some examples, the dose monitor 712 can adjust and/or weight the dose calibration data 722 to align with the patient treatment conditions.

In some examples, the treatment plan data 733 indicates an intended neutron dose to be delivered to the patient. The dose monitor 712 can determine, based on the monitoring dose 702 and a time duration of the neutron beam being directed towards the patient, that the neutron dose delivered to the patient matches or exceeds the intended neutron dose. The dose monitor 712 outputs a signal indicating that neutron dose delivered to the patient matches or exceeds the intended neutron dose. In response to determining that the neutron dose delivered to the patient matches or exceeds the intended neutron dose, the dose monitor 712 can determine that the treatment is complete, and generates output data that causes the control system 700 to stop the treatment. For example, the control system 700 outputs a control signal 726 to instruct the neutron beam system to stop outputting the neutron beam. The control system 700 can cease propagation of the neutron beam towards the patient. For example, the control system 700 outputs a control signal 726 including an instruction to cause an adjustment to the accelerator 40, such as an instruction to cause the accelerator 40 to stop propagation of the charged particle beam 61 to the target 60.

In some examples, the dose monitor 712 can adjust a duration of BNCT treatment based on the monitoring dose 702. For example, the treatment plan data 733 can include a time duration of forty minutes at a particular proton current setting. The time duration included in the treatment plan data 733 can be based on the expected neutron flux emitted from the target 60 at the particular proton current setting. In operation, the actual neutron flux emitted from the target 60 may be greater than or less than the expected neutron flux. The dose monitor 712 can use the monitoring dose 702 to increase or decrease the time duration of the treatment, so that the total dose received by the patient matches the total dose prescribed in the treatment plan data 733, within a threshold error.

The symmetry calibrator 718 can perform symmetry calibration for multiple different sets of conditions. For example, symmetry calibration can be performed as described with reference to the control system 700 of FIG. 7. The symmetry calibrator 718 can determine correction factors between the symmetry dose 704 and the monitoring dose 702, as described above with reference to FIGS. 5A and 6A. The symmetry calibrator 718 can determine correction factors between the measured doses and doses calculated using the dose simulation model 725.

Symmetry calibration data 724 generated from the symmetry calibration can be stored, e.g., in a database. The symmetry calibration data 724 can include correlations between the symmetry dose 704 and the monitoring dose 702 at each of multiple sets of conditions. In some examples, the symmetry calibration data 724 includes correction factors $F_{MD}$, $F_{SYM}$, $F_{MD}/F_{SYM}$, or any of these.

The symmetry monitor 714 can monitor symmetry of the neutron beam provided to a patient during BNCT treatment. The symmetry monitor 714 can monitor the symmetry based on the calibration data 724 generated from the calibration process. The symmetry monitor 714 can monitor the symmetry using the symmetry dose 704 output by the symmetry detector 620.

To monitor the symmetry of a neutron beam incident on a patient during BNCT treatment, the symmetry monitor 714 obtains treatment plan data 733 indicating a set of conditions at which the neutron beam is or is to be directed towards the patient during the BNCT treatment. The symmetry monitor 714 can select, from the multiple different sets of conditions represented in the symmetry calibration data 724, a first set of conditions indicative of the conditions specified by the treatment plan data 733. In some examples, the symmetry monitor 714 can select a set of conditions that satisfy similarity criteria for matching the conditions specified by the treatment plan data 733. In some examples, the symmetry monitor 714 can select a set of conditions that most closely matches the set of conditions specified by the treatment plan data 733. In some examples, the symmetry monitor 714 can select a set of conditions that is more similar to the conditions specified by the treatment plan data 733 than any other set of conditions of the multiple different sets of conditions. In some examples, the symmetry monitor 714 can monitor symmetry based on a set of conditions determined using a patient-specific or treatment-specific neutron flux simulation, e.g., a Monte Carlo simulation.

The symmetry monitor 714 obtains the symmetry calibration data 724 for the first set of conditions. During treatment, the symmetry monitor 714 obtains data indicating the symmetry dose 704 measured by a dosimeter of the symmetry detector 620. The symmetry monitor 714 can determine, using the symmetry dose 704 and the calibration data 724, whether the dose measured by a dosimeter of the symmetry detector 620 matches an expected dose within a specified threshold error.

In some examples, the symmetry monitor 714 can determine the expected dose by adjusting a calculated dose based on the set of conditions at which the treatment is performed. For example, the set of conditions specified by the treatment plan data 733 can be different from the selected set of conditions represented in the dose calibration data 722. The symmetry monitor 714 can adjust and/or weight the dose calculations to account for the difference and to align the expected dose with the set of conditions at which the treatment is being performed. In some examples, the symmetry monitor 714 can adjust and/or weight the dose calibration data 722 to align with the patient treatment conditions.

The symmetry monitor 714 can determine, based on the symmetry dose 704, that the neutron dose measured by a dosimeter of the symmetry detector 620 does not match the expected dose within the threshold error. In response, the control system 700 can perform one or more actions. For example, the control system 700 outputs a control signal 726 including an instruction to cause an adjustment to the accelerator 40, such as an instruction to stop propagation of the charged particle beam to the target 60. In some examples, the control system 700 outputs a display signal 728 to cause presentation of an alert or notification on a display 740. In some examples, the control system 700 can activate an alarm. In some examples, the control system 700 can perform one or more feedback actions, e.g., by adjusting a setting of the NBC 200 and/or of the accelerator 40 to correct or reduce the error.

In some examples, the control system 700 can perform both dose calibration and symmetry calibration and monitoring. In some examples, the control system 700 can perform dose calibration and monitoring only. In some examples, the control system 700 can perform symmetry calibration and monitoring only.

The anomaly detector 1010 monitors operations of the neutron beam system 100 during BNCT treatment. The anomaly detector 1010 can detect anomalies in various operational parameters, identify causes of anomalies, and generate output data that indicating adjustments to be made to the neutron beam system. Example anomalies, causes and adjustments are provided below.

In some examples, the anomaly detector 1010 compares the monitoring dose 702 to an expected neutron dose. The anomaly detector 101 can determine the expected neutron dose, for example, based on the proton current 1004 and the photon energy 1006. The anomaly detector 101 can determine that a difference between the monitoring dose 702 and the expected neutron dose exceeds a threshold difference. In some examples, the threshold difference is a preset neutron dose error parameter.

In some examples, the anomaly detector 1010 compares the symmetry dose 704 to an expected symmetry measure. The anomaly detector 101 can determine the expected symmetry measure, for example, based on the collimator type, the collimator position, and the patient position. The anomaly detector 101 can determine that a difference between the measured symmetry dose 704 and the expected symmetry measure exceeds a threshold difference. In some examples, the threshold difference is a preset symmetry error parameter.

Based on the output data from the anomaly detector 1010, the control system 700 generates and transmit control signals 726 that cause the adjustments. For example, the control signals 726 can include instructions to adjust components of the accelerator 40 or the HEBL 50. The control signals 726 can include instructions to adjust a patient support structure 1050, a collimator positioner 1060, a collimator selector 1070, or any of these.

The patient support structure 1050 is a mechanism that supports a patient. The patient support structure 1050 can be, for example, a table that is adjustable in height, a chair that is reclinable, or another adjustable structure. During treatment, part or all of the patient's body can be supported by the patient support structure 1050. The control system 700 outputs control signals 726 that cause adjustments of the patient support structure 1050. For example, the adjustments can include raising or lowering the patient support structure 1050, pivoting the patient support structure 1050, and tilting the patient support structure.

By adjusting the position of the patient support structure 1050, the position of the patient relative to the neutron beam is adjusted. For example, by adjusting the position of the patient support structure 1050, the patient can be moved closer to or further from the target 60, can be moved up or down relative to the axis of the neutron beam, and can be moved side to side relative to the axis of the neutron beam.

The collimator selector 1070 selects a collimator for positioning along the beam axis 203. In some examples, the neutron beam system 100 includes a set of multiple collimators. The set of collimators can include collimators of various shapes and sizes. For example, the set of collimators can include circular collimators each having a circular aperture, where the radius of each aperture is different. In some examples, a collimator can include an asymmetric aperture, and the collimator can be rotated around the beam axis to a designated angle in order to shape the beam 70. The collimator selector 1070 can select a collimator for positioning along the beam axis 203 for shaping the beam 70. The control system 700 outputs control signals 726 that cause the collimator selector 1070 to select a particular collimator to position along the beam axis.

The collimator positioner 1060 adjusts a position of one or more collimators 304. For example, the collimator positioner 1060 can raise or lower a collimator 304 with respect to the beam axis 203, can move the collimator 304 left and right with respect to the beam axis 203, can move the collimator 304 nearer to or farther from the target 60, and can increase or decrease a cone angle of the collimator 304. The control system 700 outputs control signals 726 that cause the collimator positioner 1060 to change the position of the collimator 304 that is positioned along the beam axis 203.

The control system 700 can implement any appropriate type of control processes. In some examples, the control system 700 can implement proportional control or proportional integral derivative (PID) control. Proportional control is a type of linear feedback control in which a correction is applied to the controlled variable, and the size of the correction is proportional to the difference between the desired value and the measured value. PID control is a control loop mechanism employing feedback that uses continuously modulated control. A PID controller continuously calculates an error value as the difference between a desired setpoint and a measured process variable and applies a correction based on proportional, integral, and derivative terms. In this way, PID automatically applies an accurate and responsive correction to a control function.

In some examples, a continuous control loop feedback is used to regulate the variables monitored by the control system. In some examples, the control system 700 outputs control signals 126 including setpoints for components of the neutron beam system 100. The components adjust to the prescribed setpoints in response to receiving the control signals 126. In some examples, the control system 700 implements On-Off control.

In some examples, in addition to or instead of outputting the control signals 726, the control system 700 outputs a display signal 728 to present a notification on the display 740, outputs an alarm signal 1028 to activate an alarm 1012, or both.

The control system 700 receives sensor data from sensors that are configured to monitor a parameter of the neutron beam system 100. In some examples, the sensors output a value of the monitored parameter to the control system 700. In some examples, the control system 700 obtains or evaluates the sensor data in response to determining that the difference between the measured neutron dose and the expected neutron dose exceeds a threshold difference. In some examples, the control system 700 obtains or evaluates the sensor data in response to determining that the difference between the measured symmetry dose and the expected symmetry measure exceeds a threshold difference.

The sensor data received from the sensors can include the monitoring dose 702 received from the monitoring dosimeter 410-1 that monitors a neutron flux parameter. The sensor data received from the sensors can include the symmetry dose 704 received from the symmetry detector 620 that monitors a symmetry parameter. The sensor data can include the target sensor data 708 received from the target sensor 760 that monitors a parameter of the target 60, such as a temperature of the target 60. The sensor data can include the proton current 1004 received from the current monitor 54 that monitors a proton current parameter. The sensor data can include the photon energy 1006 received from the photon detector 1002 that monitors a photon parameter.

The control system 700 can determine expected values of parameters of the neutron beam system. For example, the control system 700 can determine expected values of parameters including the neutron flux parameter, the symmetry parameter, the parameter of the target, the proton current, the photon energy, the photon parameter, or any combination of these. In some examples, the control system 700 determines the expected values based on the treatment plan data 733, based on calibration data (e.g., dose calibration data 722, symmetry calibration data 724), or both.

In some examples, the treatment plan data 733 can include a proton current setting and an accelerator energy setting. The control system 700 can determine an expected value for the proton current 1004 based on the proton current setting. The control system 700 can determine an expected value for the monitoring dose 702 and the photon energy 1006 based on the proton current setting and the dose calibration data 722.

In some examples, the treatment plan data 733 can include a proton current setting, an accelerator energy setting, and a time duration of treatment. The control system 700 can determine an expected value for target temperature based on the proton current setting, the accelerator energy setting, and the time duration of treatment. For example, the control system 700 can store data indicating expected target temperature values for various settings and time durations.

In some examples, the treatment plan data 733 can include a position of the patient and a type of collimator. The control system 700 can determine an expected value of the symmetry dose 704 based on the position of the patient, the type of collimator, and the symmetry calibration data 724.

The anomaly detector 1010 can detect anomalies based on evaluating operational parameters (e.g., a neutron flux parameter, a symmetry parameter, a parameter of the target, a proton current, a photon energy, a photon parameter). In some examples, the anomaly detector 1010 determines whether an anomaly is occurring by comparing the value of a parameter to an expected value of the parameter, and determining whether the difference between the value of the parameter and the expected value of the parameter exceeds a threshold difference. In some examples, the anomaly detector 1010 determines whether an anomaly is occurring by comparing the value of a parameter to an expected range of the parameter, and determines whether the parameter is within the expected range. In some examples, the anomaly detector 1010 determines whether an anomaly is occurring based on two or more parameters differing from their respective expected values and/or ranges.

In some examples, in response to determining that the difference between the value of a parameter and an expected value of a parameter exceeds a threshold difference, the control system 700 can perform an action. For example, the control system 700 can perform an action such as sending a display signal 728 to the display 740 to present an alert or notification to a user, sending an alarm signal 1028 to activate an alarm 1012, and/or sending control signals 726 to adjust a component of the neutron beam system. In some examples, the action includes sending a control signal 726 that causes the neutron beam system to cease outputting the neutron beam.

In some examples, feedback to correct an action may include human intervention. For example, the control system 700 may perform an action of sending a display signal 728 to the display 740 to present a notification to a user indicating that the patient position is too low with respect to the beam. The user may manually adjust the patient support structure 1050 to raise the position of the patient. The control system 700 can evaluate the parameters with the adjusted position of the patient support structure, to determine if an anomaly still exists, or if the human intervention has corrected the anomaly. In response to determining that the anomaly is corrected, the control system 700 can send a display signal 728 to the display 740 to present a notification to the user that the patient is in the correct position. In response to determining that an anomaly still exists, the control system 700 can send a display signal 728 to the display 740 to present a notification to the user that the anomaly exists, and whether the anomaly is the same anomaly (e.g., patient position is too low) or is a different anomaly (e.g., patient position is too high).

In some examples, in response to determining that the difference between the value of a parameter and an expected value of a parameter exceeds a threshold difference, the control system 700 can obtain and/or evaluate additional data to determine a likely cause of the difference between the measured neutron dose and the expected neutron dose. The control system 700 can perform an action based on the determined cause of the difference.

The cause of the difference between the value of a parameter and an expected value of a parameter can be a setting of a component of the neutron beam system 100. In some examples, the control system 700 can store data indicating likely causes of unexpected parameter values. The control system 700 can compare the sensor data to the stored data to identify likely causes of unexpected parameter values.

In some examples, the control system 700 can determine likely causes of unexpected parameter values by identifying patterns and/or coincidences in sensor data. In an example scenario, the control system 700 may determine that the value of the monitoring dose 702 is within a threshold difference of the expected value of monitoring dose, and that the value of the symmetry dose 704 is not within a threshold difference of the expected value of symmetry dose. The control system 700 can determine, using stored data indicating likely causes of unexpected parameters, that since the value of the monitoring dose 702 is within a threshold difference of the expected value of monitoring dose, the unexpected value of the symmetry dose 704 is likely caused by a setting of the charged particle beam 61 (e.g., beam focus, raster pattern, beam directionality) and is likely not caused by a condition of the target. In another example scenario, the control system 700 may determine that the value of the symmetry dose 704 is within a threshold difference of the expected value of symmetry dose, and that the value of the monitoring dose 702 is not within a threshold difference of the expected value of monitoring dose. The control system 700 can determine, using stored data indicating likely causes of unexpected parameters, that since the value of the symmetry dose 704 is within a threshold difference of the expected value of symmetry dose, the unexpected value of the monitoring dose 702 is likely caused by a condition of the target 60 (e.g., reduced thickness, lack of lithium), and is likely not caused by a setting of the charged particle beam 61.

In some examples, the cause of the difference between a value of a parameter and an expected value of the parameter is a setting of the accelerator 40, such as an energy of the accelerator 40. For example, the energy of the accelerator 40 may be too high or too low, causing unexpected values of monitoring dose 702, target sensor data 708, proton current 1004, photon energy 1006, or any of these.

The cause of the difference between the value of a parameter and an expected value of a parameter can be condition of the charged particle beam 61. For example, the cause can be a directionality of the charged particle beam 61, a focus of the charged particle beam 61, a raster pattern of the charged particle beam 61, or any combination of these. For example, the charged particle beam 61 may be directed to a part of the neutron-generating target that is lacking lithium, causing an unexpectedly low monitoring dose 702, an unexpected value of symmetry dose 704, an unexpected value of target sensor data 708, or any of these. The focus of the charged particle beam 61 may be too wide or too narrow, causing an unexpected value of target sensor data 708, monitoring dose 702, photon energy 1006, or any of these. The raster pattern of the charged particle beam 61 may be too large or too small, or have a frequency that is too high or too low, causing unexpected values of target sensor data 708.

The cause of the difference between the value of a parameter and an expected value of a parameter can be a condition of the target 60, such as a thickness and/or uniformity of the target 60. For example, the neutron-generating target may be degraded in thickness, causing unexpected values of monitoring dose 702, photon energy 7006, target sensor data 708, or any of these. The degradation in thickness may be non-uniform, causing unexpected values of symmetry dose 704.

The cause of the difference between the value of a parameter and an expected value of a parameter can be a type of a collimator located between the target 60 and the patient, a position of the collimator located between the target 60 and the patient, or both. For example, the type of collimator positioned along the beam axis might not be of adequate size or shape to support the treatment plan data 733, causing unexpected values of monitoring dose 702, symmetry dose 704, and/or photon energy 1006. The collimator positioned along the beam axis might be positioned incorrectly relative to the beam axis, causing unexpected values of monitoring dose 702, symmetry dose 704, and/or photon energy 1006.

The cause of the difference between the value of a parameter and an expected value of a parameter can be a position of the patient. For example, the patient may be positioned too near to or far from the target 60, the patient may be tilted or angled incorrectly, and/or the patient may be positioned incorrectly relative to the beam axis, causing unexpected values of symmetry dose 704.

The control system 700 can perform actions based on the cause of the unexpected parameter values. For example, the control system 700 generates and transmit control signals 726 that cause adjustments to components of the neutron beam system. For example, the control signals 726 can include instructions to adjust the accelerator 40, the HEBL 50, the patient support structure 1050, the collimator positioner 1060, the collimator selector 1070, or any combination of these In response to determining that the cause of the difference between a value of a parameter and an expected value of the parameter is a setting of the accelerator 40, the control system 700 outputs control signals 726 to adjust the setting of the accelerator 40. For example, the control signals 726 can include an instruction to raise or lower an energy setting of the accelerator 40.

In response to determining that the cause of the difference between a value of a parameter and an expected value of the parameter is a condition of the charged particle beam 61, the control system 700 outputs control signals 726 to adjust settings of the accelerator 40, the HEBL 50, or both. Control signals 726 output to the HEBL 50 can cause adjustments to a field of an electromagnet of the HEBL 50 and to a focus of a quadrupole magnet 72 of the HEBL 50.

In response to determining that the cause of the difference between a value of a parameter and an expected value of the parameter is a directionality of the charged particle beam 61, the control system 700 outputs control signals 726 to the HEBL 50 to adjust the directionality of the charged particle beam 61. Control signals 726 output to the HEBL 50 can cause adjustments to a field of an electromagnet of the HEBL 50, to a focus of a quadrupole magnet 72 of the HEBL 50, or both. In some examples, the control signals 726 can cause the HEBL 50 to adjust the directionality of the charged particle beam 61 to aim the beam at a portion of the target 60 with greater lithium thickness than other portions of the target.

In response to determining that the cause of the difference between a value of a parameter and an expected value of the parameter is a focus of the charged particle beam 61, the control system 700 outputs control signals 726 to the HEBL 50 to adjust the focus of the charged particle beam 61. For example, the control signals 726 can cause the HEBL 50 to narrow or widen the focus of the charged particle beam 61.

In response to determining that the cause of the difference between a value of a parameter and an expected value of the parameter is a raster pattern of the charged particle beam 61, the control system 700 outputs control signals 726 to adjust the raster pattern of the charged particle beam 61. For example, the control signals 726 can cause the HEBL 50 to increase or decrease a frequency of the raster pattern.

In response to determining that the cause of the difference between the value of a parameter and an expected value of a parameter is a condition of the target 60, the control system 700 outputs control signals 726 to adjust a setting of the accelerator 40, the HEBL 50, or both. For example, a portion of the target 60 where the charged particle beam 61 is incident on the target 60 may be degraded in thickness. The control signals 126 can cause an increase in energy of the accelerator 40 and/or a change in the focus of a quadrupole magnet 72 of the HEBL 50, in order to compensate for the degradation in target thickness. In some examples, the control signals 126 can cause the HEBL to change a directionality of the charged particle beam 61 in order to aim the charged particle beam 61 at a different portion of the target 60 with a greater thickness.

In response to determining that the cause of the difference between a value of a parameter and an expected value of the parameter is a type of collimator, the control system 700 outputs control signals 726 to the collimator selector 1070 to change the type of collimator. For example, the control signals 726 can cause the collimator selector 1070 to select a collimator with an asymmetric aperture instead of a collimator with a symmetric aperture. The collimator selector 1070 can position the selected collimator between the target 60 and the patient.

In response to determining that the cause of the difference between a value of a parameter and an expected value of the parameter is a position of a collimator, the control system 700 outputs control signals 726 to the collimator positioner

1060 to adjust the position of the collimator. For example, the control signals 726 can cause the collimator positioner 1060 to rotate the collimator and/or to move the collimator laterally relative to the beam axis.

In response to determining that the cause of the difference between a value of a parameter and an expected value of the parameter is a position of a patient, the control system 700 outputs control signals 726 to the patient support structure 1050 to change the position of the patient support structure 1050. For example, the control signals 726 can cause the patient support structure 1050 to raise or lower the patient, to move the patient towards or away from the target 60, or to tilt the patient.

In some examples, in response to determining that the cause of the difference between a value of a parameter and an expected value of the parameter is a position of a patient, the control system 700 can adjust a component of the system 100 other than the patient support structure 1050 to accommodate the position of the patient. For example, the anomaly detector 1010 can determine that, with the proton current at an initial level, the patient has moved from an initial position to an adjusted position that is too close to the target 60. Instead of adjusting the patient support structure 1050 to move the patient further from the target 60, the control signals 726 can cause proton current 1004 to adjust from the initial level to an adjusted, lower level, so that the intensity of the neutron beam delivered to the patient's adjusted position by the lowered proton current is the same as the initial intensity of the neutron beam delivered to the patient's initial position by the initial proton current. In this way, the control system 700 can adjust a parameter of the system 700 (e.g., proton current) in response to detecting changes or anomalies external to the system 700 (e.g., patient movement).

FIG. 8 depicts a flow diagram of an example process 800 for calibrating a monitoring dosimeter using a reference dosimeter, as illustrated in FIG. 5A, and using the calibrated monitoring dosimeter to monitor neutron dose delivered to a patient during BNCT treatment, as illustrated in FIG. 5B. The process 800 can be performed by one or more computer systems, e.g., by the control system 700 of the system 100. The process 800 includes obtaining data indicating a first neutron flux measured by a monitoring dosimeter (802). For example, the dose calibrator 716 obtains the monitoring dose 702 measured by the monitoring dosimeter 410-1. The process 800 includes obtaining data indicating a second neutron flux measured by a reference dosimeter (804). For example, the dose calibrator 716 obtains the reference dose 706 measured by the reference dosimeter 410-2, shown in FIG. 5A. In some examples, the first neutron flux and the second neutron flux are measured simultaneously or near simultaneously. The process 800 includes storing calibration data including a correlation between the first neutron flux and the second neutron flux (806). For example, the dose calibrator 716 generates dose calibration data 722 and stores the dose calibration data 722 in a database. The process 800 includes using the calibration data and a neutron flux measured by the monitoring dosimeter to determine a neutron flux incident on the patient (808). For example, the dose monitor 712 uses the dose calibration data 722 and the monitoring dose 702 measured by the monitoring dosimeter 410-1 to determine a neutron flux incident on the patient 522, as shown in FIG. 5B.

FIG. 9 depicts a flow diagram of an example process 900 for calibrating a symmetry detector using a monitoring dosimeter, as illustrated in FIG. 6A, and using the calibrated symmetry detector to monitor symmetry of a neutron beam delivered to a patient during BNCT treatment, as shown in FIG. 6B. The process 900 can be performed by one or more computer systems, e.g., by the control system 700 of the system 100. The process 900 includes obtaining data indicating a first neutron flux measured by a dosimeter of a symmetry monitoring system (902). For example, the symmetry calibrator 718 obtains the symmetry dose 704 measured by the symmetry detector 620, shown in FIG. 6A. The process 900 includes obtaining data indicating a second neutron flux measured by a monitoring dosimeter (904). For example, the symmetry calibrator 718 obtains the monitoring dose 702 measured by the monitoring dosimeter 410-1, shown in FIG. 6A. In some examples, the first neutron flux and the second neutron flux are measured simultaneously or near simultaneously. The process 900 includes storing calibration data including a correlation between the first neutron flux and the second neutron flux (906). For example, the symmetry calibrator 718 generates symmetry calibration data 724 and stores the dose calibration data 724 in a database. The process 900 includes using the calibration data and a neutron flux measured by the monitoring dosimeter to determine an expected neutron flux measured by the dosimeter of the symmetry monitoring system (908). For example, the symmetry monitor 714 uses the symmetry calibration data 718 and the monitoring dose 702 to determine an expected neutron flux measured by the symmetry detector 620. The process 900 includes, based on the expected neutron flux measured by the dosimeter of the symmetry monitoring system, monitoring the neutron flux incident on the patient (910). For example, the symmetry monitor 714 can compare the expected neutron flux measured by the symmetry detector 620 to the actual neutron flux measured by the symmetry detector 620 to detect symmetry anomalies in beam reflection from the patient 622, shown in FIG. 6B.

Figure 10:
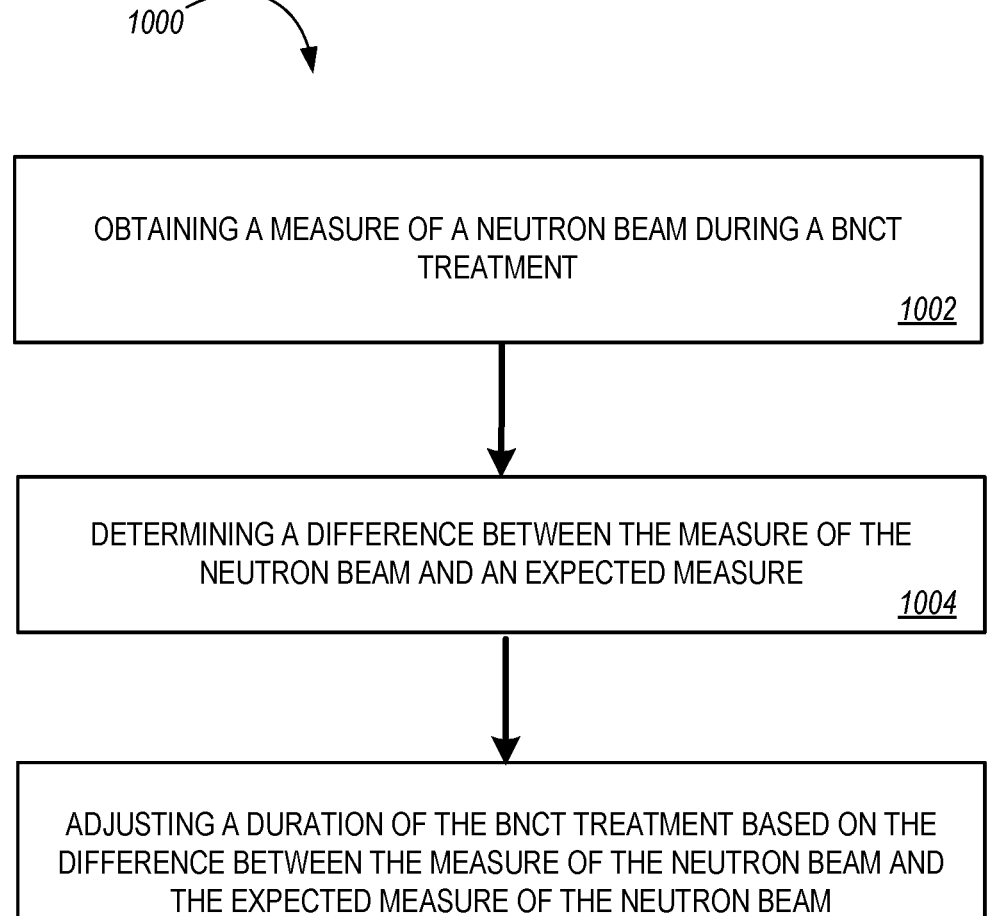
FIG. 10 shows a flow diagram of an example process for monitoring neutron dose delivered to a patient during BNCT treatment in accordance with the present disclosure.

FIG. 10 depicts a flow diagram of an example process 1000 for monitoring neutron dose delivered to a patient during BNCT treatment. The process 1000 can be performed by one or more computer systems, e.g., by the control system 700. The process 1000 includes obtaining a measure of a neutron beam during a BNCT treatment (1002). The process 1000 includes determining a difference between the measure of the neutron beam and an expected measure (1004). The process 1000 includes adjusting a duration of the BNCT treatment based on the difference between the measure of the neutron beam and the expected measure of the neutron beam (1006).

Figure 11:
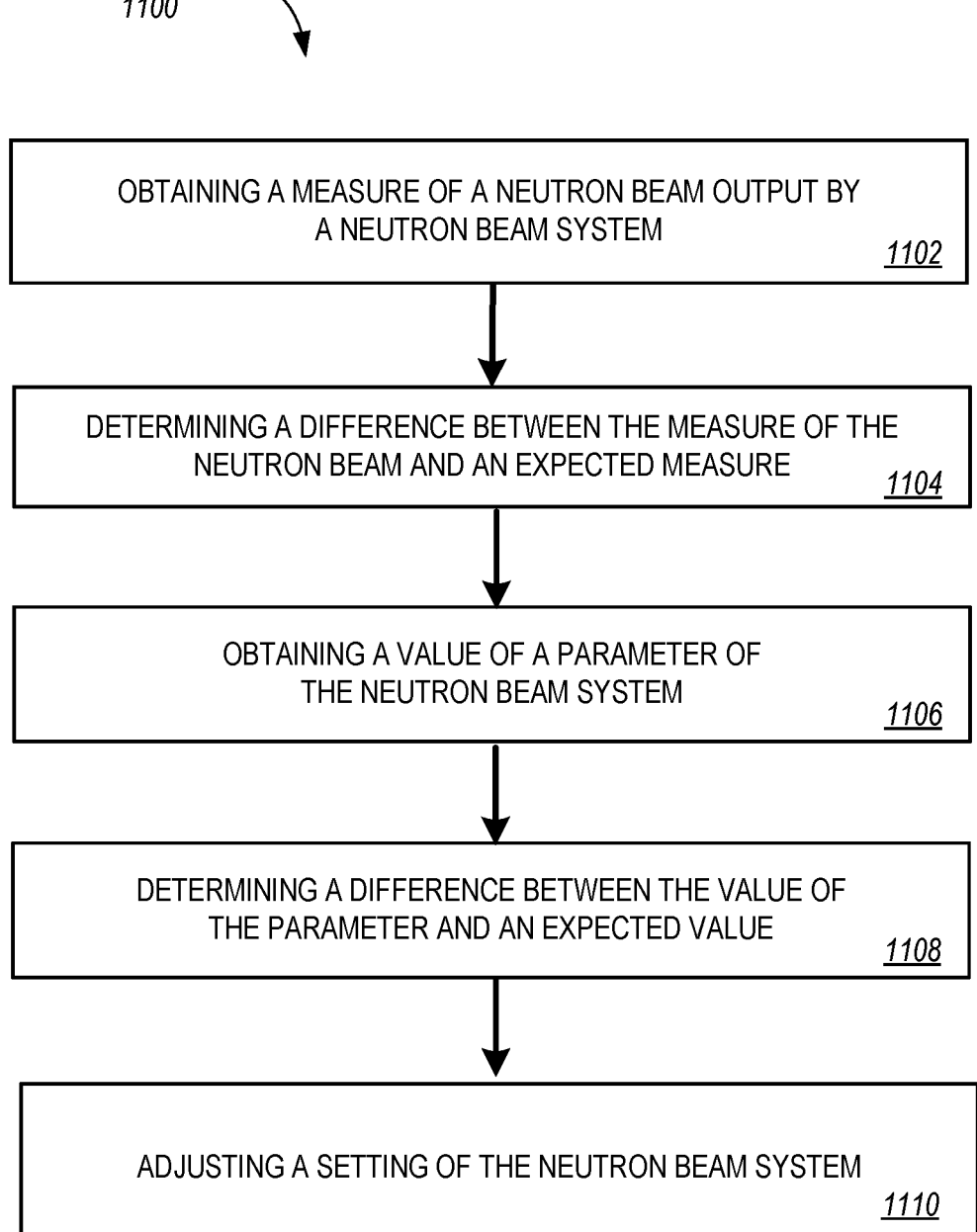
FIG. 11 shows a flow diagram of an example process for controlling a neutron beam system during BNCT treatment in accordance with the present disclosure.

FIG. 11 depicts a flow diagram of an example process 1100 for controlling a neutron beam system during BNCT treatment. The process 1100 can be performed by one or more computer systems, e.g., by the control system 700. The process 1100 includes obtaining a measure of a neutron beam output by a neutron beam system (1102). For example, the measure of the neutron beam can be the monitoring dose 702 measured by the monitoring dosimeter 410-1. The process 1100 includes determining a difference between the measure of the neutron beam and an expected measure (1104). For example, the dose monitor 712 can determine a difference between the monitoring dose 702 and an expected monitoring dose and can determine that the monitoring dose 702 is lower than the expected monitoring dose. The process 1100 includes obtaining a value of a parameter of the neutron beam system (1106). For example, the control system 700 can obtain a value of an energy setting of the accelerator 40. The process 1100 includes determining a difference between the value of the parameter and an expected value (1108). For example, anomaly detector 1010 can determine a difference between the energy setting of the accelerator 40 and an expected value of the energy setting, and can determine that the energy setting of the accelerator 40 is less than the expected value of the energy setting. The process 1100 includes adjusting a setting of the neutron beam system (1110). For example, the control system 700 can send a control signal 726 to increase the energy setting of the accelerator 40.0

Although described with respect to BNCT application, embodiments described herein are usable in non-BNCT applications. For example, the embodiments described herein can be usable in external beam radiation therapy applications such as proton beam therapy applications, carbon ion therapy applications, fast neutron therapy applications, and electron therapy applications.

Figure 12:
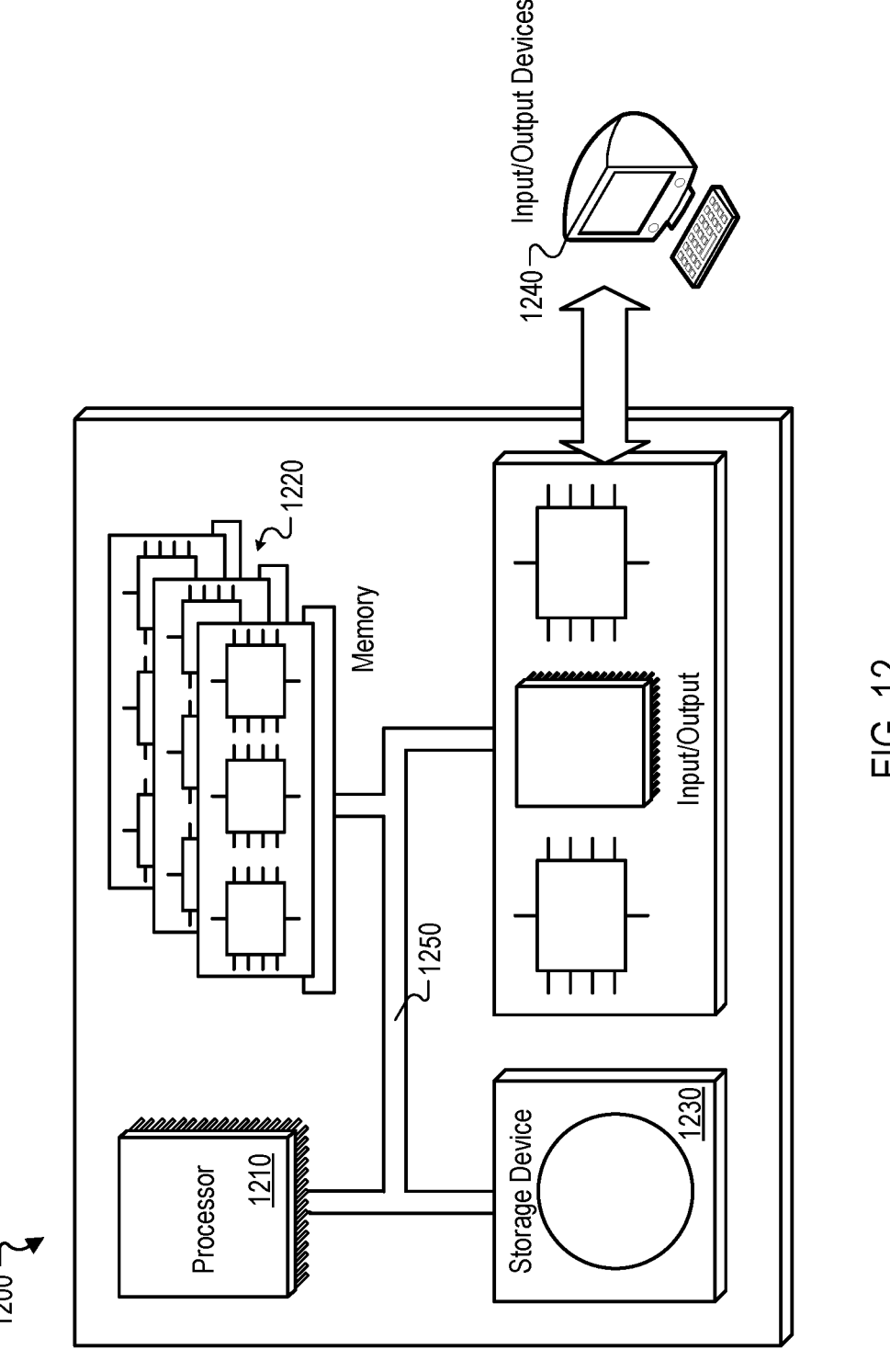
FIG. 12 shows a schematic diagram of a computer system that can be applied to any of the computer-implemented methods and other techniques described herein in accordance with the present disclosure.

FIG. 12 is a schematic diagram of a computer system 1200. The system 1200 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 1200) and their structural equivalents, or in combinations of one or more of them. The system 1200 is intended to include various forms of digital computers, such as laptops, desktops, workstations, personal digital assistants, servers, blade servers, mainframes, and other appropriate computers, including vehicles installed on base units or pod units of modular vehicles. The system 1200 can also include mobile devices, such as personal digital assistants, cellular telephones, smartphones, and other similar computing devices. Additionally, the system can include portable storage media, such as Universal Serial Bus (USB) flash drives. For example, the USB flash drives can store operating systems and other applications. The USB flash drives can include input/output components, such as a wireless transducer or USB connector that can be inserted into a USB port of another computing device.

The system 1200 includes a processor 1210, a memory 1220, a storage device 1230, and an input/output device 1240. Each of the components 1210, 1220, 1230, and 1240 are interconnected using a system bus 1250. The processor 1210 is capable of processing instructions for execution within the system 1200. The processor can be designed using any of a number of architectures. For example, the processor 1210 can be a CISC (Complex Instruction Set Computers) processor, a RISC (Reduced Instruction Set Computer) processor, or a MISC (Minimal Instruction Set Computer) processor.

In one implementation, the processor 1210 is a single-threaded processor. In another implementation, the processor 1210 is a multi-threaded processor. The processor 1210 is capable of processing instructions stored in the memory 1220 or on the storage device 1230 to display graphical information for a user interface on the input/output device 1240.

The memory 1220 stores information within the system 1200. In one implementation, the memory 1220 is a computer-readable medium. In one implementation, the memory 1220 is a volatile memory unit. In another implementation, the memory 1220 is a non-volatile memory unit.

The storage device 1230 is capable of providing mass storage for the system 1200. In one implementation, the storage device 1230 is a computer-readable medium. In various different implementations, the storage device 1230 can be a floppy disk device, a hard disk device, an optical disk device, or a tape device.

The input/output device 1240 provides input/output operations for the system 1200. In one implementation, the input/output device 1240 includes a keyboard and/or pointing device. In another implementation, the input/output device 1240 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as an LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a frontend component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

In addition to the embodiments described above, the following embodiments are also innovative.

Embodiment 1 is a method, comprising: obtaining a measured neutron flux output by a dosimeter configured to monitor a neutron flux of a neutron beam during a boron neutron capture therapy (BNCT) treatment on a patient; and performing one or more actions based on the measured neutron flux.

Embodiment 2 is the method of embodiment 1, comprising: determining, based on the measured neutron flux, that a neutron dose delivered to the patient matches or exceeds an intended neutron dose to be delivered to the patient; and in response to determining that the neutron dose delivered to the patient matches or exceeds the intended neutron dose, transmitting an instruction to a neutron beam system outputting the neutron beam to cease outputting the neutron beam Embodiment 3 is the method of any one of embodiments 1 or 2, comprising: determining that a difference between the measured neutron flux and an expected neutron flux exceeds a first threshold difference; and in response to determining that the difference between the measured neutron flux and the expected neutron flux exceeds the first threshold difference, performing the one or more actions.

Embodiment 4 is the method of embodiment 3, wherein performing the one or more actions comprises: adjusting a duration of the boron neutron capture therapy treatment based on the difference between the measured neutron flux and the expected neutron flux.

Embodiment 5 is the method of embodiment 4, wherein neutrons in the neutron beam are emitted from a neutron-generating target in response to a charged particle beam incident on the neutron-generating target.

Embodiment 6 is the method of embodiment 5, comprising: determining the expected neutron flux based on a current of the charged particle beam.

Embodiment 7 is the method of any one of embodiments 5 or 6, comprising: determining the expected neutron flux based on an energy of the charged particle beam.

Embodiment 8 is the method of any one of embodiments 3 to 7, wherein neutrons in the neutron beam are emitted from a neutron-generating target in response to a charged particle beam incident on the neutron-generating target, the method comprising: obtaining sensor data from a sensor configured to monitor a parameter of a neutron beam system outputting the neutron beam; determining, using the sensor data, a cause of the difference between the measured neutron flux and the expected neutron flux; and performing the one or more actions based on the cause of the difference between the measured neutron flux and the expected neutron flux.

Embodiment 9 is the method of embodiment 8, wherein the parameter is selected from the group consisting of: a current of the charged particle beam; an energy of the charged particle beam; a temperature of the neutron-generating target; a photon flux emitted from the neutron-generating target; and a symmetry of the neutron beam.

Embodiment 10 is the method of any one of embodiments 8 or 9, wherein the cause of the difference between the measured neutron flux and the expected neutron flux comprises one of the group consisting of: an energy of an accelerator configured to accelerate the charged particle beam towards the neutron-generating target; a directionality of the charged particle beam; a focus of the charged particle beam; a raster pattern of the charged particle beam; a thickness of the neutron-generating target; a type of a collimator located between the neutron-generating target and the patient; a position of the collimator located between the neutron-generating target and the patient; and a position of the patient.

Embodiment 11 is the method of any one of embodiment 8 to 10, wherein the one or more actions is selected from the group consisting of: adjusting an energy of an accelerator configured to accelerate the charged particle beam towards the neutron-generating target; adjusting a directionality of the charged particle beam; adjusting a focus of the charged particle beam; adjusting a raster pattern of the charged particle beam; adjusting a type of a collimator located between the neutron-generating target and the patient; adjusting a position of the collimator located between the neutron-generating target and the patient; and adjusting a position of a structure supporting the patient.

Embodiment 12 is the method of any one of embodiments 8 to 11, wherein: the parameter of the neutron beam system comprises a current of the charged particle beam or an energy of the charged particle beam; the cause of the difference between the measured neutron flux and the expected neutron flux comprises a setting of an accelerator configured to accelerate the charged particle beam; and the one or more actions comprise adjusting the setting of the accelerator.

Embodiment 13 is the method of any one of embodiments 8 to 12, wherein: the parameter of the neutron beam system comprises a temperature of the neutron-generating target; the cause of the difference between the measured neutron flux and the expected neutron flux comprises a directionality of the charged particle beam; and the one or more actions comprise adjusting the directionality of the charged particle beam.

Embodiment 14 is the method of any one of embodiments 8 to 13, wherein: the parameter of the neutron beam system comprises a temperature of the neutron-generating target; the cause of the difference between the measured neutron flux and the expected neutron flux comprises a focus of the charged particle beam; and the one or more actions comprise adjusting the focus of the charged particle beam.

Embodiment 15 is the method of any one of embodiments 8 to 14, wherein: the parameter of the neutron beam system comprises a temperature of the neutron-generating target; the cause of the difference between the measured neutron flux and the expected neutron flux comprises a raster pattern of the charged particle beam; and the one or more actions comprise of adjusting the raster pattern of the charged particle beam.

Embodiment 16 is the method of any one of embodiments 8 to 15, wherein: the parameter of the neutron beam system comprises a temperature of the neutron-generating target; the cause of the difference between the measured neutron flux and the expected neutron flux comprises a thickness of the neutron-generating target; and the one or more actions comprise at least one of adjusting a directionality of the charged particle beam, adjusting a focus of the charged particle beam, or adjusting a raster pattern of the charged particle beam.

Embodiment 17 is the method of any one of embodiments 8 to 16, wherein: the parameter of the neutron beam system comprises a photon flux emitted from the neutron-generating target; the cause of the difference between the measured neutron flux and the expected neutron flux comprises a setting of an accelerator configured to accelerate the charged particle beam; and the one or more actions comprise adjusting the setting of the accelerator.

Embodiment 18 is the method of any one of embodiments 8 to 17, wherein: the parameter of the neutron beam system comprises a symmetry of the neutron beam; the cause of the difference between the measured neutron flux and the expected neutron flux comprises a position of the patient; and the one or more actions comprise adjusting a position of a structure supporting the patient.

Embodiment 19 is the method of any one of embodiments 8 to 18, wherein: the parameter of the neutron beam system comprises a symmetry of the neutron beam; the cause of the difference between the measured neutron flux and the expected neutron flux comprises a type of a collimator located between the neutron-generating target and the patient; and the one or more actions comprise adjusting the type of the collimator located between the neutron-generating target and the patient.

Embodiment 20 is the method of any one of embodiments 8 to 19, wherein: the parameter of the neutron beam system comprises a symmetry of the neutron beam; the cause of the difference between the measured neutron flux and the expected neutron flux comprises a position of a collimator located between the neutron-generating target and the patient; and the one or more actions comprise adjusting the position of the collimator located between the neutron-generating target and the patient.

Embodiment 21 is the method of any one of embodiment 3 to 20, comprising: obtaining, from a sensor configured to monitor a parameter of a neutron beam system outputting the neutron beam, a value of the parameter; determining that a difference between the value of the parameter and an expected value of the parameter exceeds a second threshold difference; and performing the one or more actions in response to (i) determining that the difference between the measured neutron flux and the expected neutron flux exceeds the first threshold difference and (ii) determining that the difference between the value of the parameter and the expected value of the parameter exceeds the second threshold difference.

Embodiment 22 is the method of any one of embodiments 3 to 21, comprising: obtaining a symmetry measure output by a symmetry monitor configured to monitor a symmetry of the neutron beam during the boron neutron capture therapy treatment on the patient; determining a difference between the symmetry measure of the neutron beam and an expected symmetry measure of the neutron beam; and performing the one or more actions (i) in response to determining that the difference between the measured neutron flux and the expected neutron flux exceeds the first threshold difference and (ii) based on the difference between the symmetry measure of the neutron beam and the expected symmetry measure of the neutron beam.

Embodiment 23 is the method of embodiment 22, wherein: the neutron beam propagates along an axis extending in an axial direction from a neutron-generating target towards the patient and has a beam radius extending in a radial direction orthogonal to the axial direction; and the symmetry monitor comprises a plurality of dosimeters that are each positioned at an axial location between the neutron-generating target and the patient and are offset from the axis in the radial direction by a distance equal to or less than the beam radius.

Embodiment 24 is the method of any one of embodiments 1 to 23, wherein neutrons in the neutron beam are emitted from a neutron-generating target in response to a charged particle beam incident on the neutron-generating target.

Embodiment 25 is the method of embodiment 24, the one or more actions comprising adjusting a directionality, a focus, or a raster pattern of the charged particle beam.

Embodiment 26 is the method of any one of embodiments 24 or 25, the one or more actions comprising adjusting a setting of a high-energy beamline configured to transport the charged particle beam to the neutron-generating target.

Embodiment 27 is the method of embodiment 26, wherein adjusting the setting of the high-energy beamline comprises adjusting a field of an electromagnet of the high-energy beamline.

Embodiment 28 is the method of any one of embodiments 26 or 27, wherein adjusting the setting of the high-energy beamline comprises adjusting a focus of a quadrupole magnet of the high-energy beamline.

Embodiment 29 is the method of any one of embodiments 24 to 28, the one or more actions comprising adjusting a position of a collimator located between the neutron-generating target and the patient.

Embodiment 30 is the method of any one of embodiments 24 to 29, the one or more actions comprising adjusting a type of collimator located between the neutron-generating target and the patient.

Embodiment 31 is the method of any one of embodiments 24 to 30, comprising: obtaining, from an energy sensor, an energy of the charged particle beam; and performing the one or more actions based at least in part on the energy of the charged particle beam.

Embodiment 32 is the method of any one of embodiments 24 to 31, comprising: obtaining, from a temperature sensor, a temperature of the neutron-generating target; and performing the one or more actions based at least in part on the temperature of the neutron-generating target.

Embodiment 33 is the method of any one of embodiments 24 to 32, comprising: obtaining, from a current monitor, a current of the charged particle beam; and performing the one or more actions based at least in part on the current of the charged particle beam.

Embodiment 34 is the method of any one of embodiments 24 to 33, comprising: obtaining a measured photon flux from a photon detector configured to detect photons emitted from the neutron-generating target; and performing the one or more actions based at least in part on the measured photon flux.

Embodiment 35 is the method of any one of embodiments 24 to 34, the one or more actions comprising adjusting a setting of an accelerator configured to accelerate the charged particle beam towards the neutron-generating target.

Embodiment 36 is the method of any one of embodiments 1 to 35, wherein the patient is supported by a structure, the one or more actions comprising adjusting a position of the structure.

Embodiment 37 is the method of any one of embodiments 1 to 36, the one or more actions comprising providing a notification for presentation by a display.

Embodiment 38 is the method of any one of embodiments 1 to 37, the one or more actions comprising activating an alarm.

Embodiment 39 is the method of any one of embodiments 1 to 38, the one or more actions comprising transmitting an instruction to a neutron beam system outputting the neutron beam to cease outputting the neutron beam.

Embodiment 40 is the method of any one of embodiments 1 to 39, the one or more actions comprising adjusting a setting of a component of a neutron beam system outputting the neutron beam.

Embodiment 41 is the method of any one of embodiments 1 to 40, the one or more actions comprising adjusting at least one parameter of a beam shaping system for shaping the neutron beam.

Embodiment 42 is a non-transitory computer-readable medium storing software comprising instructions executable by one or more computers which, upon such execution, cause the one or more computers to perform operations comprising the method of any one of embodiments 1 to 41.

Embodiment 43 is a system comprising: one or more computers; and one or more storage devices storing instructions that are operable, when executed by the one or more computers, to cause the one or more computers to perform operations comprising the method of any one of embodiments 1 to 41.

Embodiment 44 is a method, comprising: obtaining a symmetry measure output by a symmetry monitor configured to monitor a symmetry of a neutron beam during a boron neutron capture therapy treatment on a patient; and performing one or more actions based on the symmetry measure.

Embodiment 45 is the method of embodiment 44, wherein: the neutron beam propagates along an axis extending in an axial direction from a neutron-generating target towards the patient and has a beam radius extending in a radial direction orthogonal to the axial direction; and the symmetry monitor comprises a plurality of dosimeters that are each positioned at an axial location between the neutron-generating target and the patient and are offset from the axis in the radial direction by a distance equal to or less than the beam radius, the plurality of dosimeters being arranged at different azimuthal positions around the axis.

Embodiment 46 is the method of any one of embodiments 44 or 45, comprising: determining that a difference between the symmetry measure and an expected symmetry measure exceeds a first threshold difference; and in response to determining that the difference between the symmetry measure and the expected symmetry measure exceeds the first threshold difference, performing the one or more actions.

Embodiment 47 is the method of embodiment 46, wherein neutrons in the neutron beam are emitted from a neutron-generating target in response to a charged particle beam incident on the neutron-generating target, the method comprising: obtaining sensor data from a sensor configured to monitor a parameter of a neutron beam system outputting the neutron beam; determining, using the sensor data, a cause of the difference between the symmetry measure and the expected symmetry measure; and performing the one or more actions based on the cause of the difference between the symmetry measure and the expected symmetry measure.

Embodiment 48 is the method of embodiment 47, wherein the parameter is selected from the group consisting of: a temperature of the neutron-generating target; a photon flux emitted from the neutron-generating target; and a neutron flux of the neutron beam.

Embodiment 49 is the method of any one of embodiments 47 or 48, wherein the cause of the difference between the symmetry measure and the expected symmetry measure comprises one of the group consisting of: a directionality of the charged particle beam; a raster pattern of the charged particle beam; a uniformity of the neutron-generating target; a type of a collimator located between the neutron-generating target and the patient; a position of the collimator located between the neutron-generating target and the patient; and a position of the patient.

Embodiment 50 is the method of any one of embodiments 47 to 49, wherein the one or more actions is selected from the group consisting of: adjusting a directionality of the charged particle beam; adjusting a raster pattern of the charged particle beam; adjusting a type of a collimator located between the neutron-generating target and the patient; adjusting a position of the collimator located between the neutron-generating target and the patient; and adjusting a position of a structure supporting the patient.

Embodiment 51 is the method of any one of embodiments 47 to 50, wherein: the parameter of the neutron beam system comprises a temperature of the neutron-generating target; the cause of the difference between the symmetry measure and the expected symmetry measure comprises a directionality of the charged particle beam; and the one or more actions comprise adjusting the directionality of the charged particle beam.

Embodiment 52 is the method of any one of embodiments 47 to 51, wherein: the parameter of the neutron beam system comprises a temperature of the neutron-generating target; the cause of the difference between the symmetry measure and the expected symmetry measure comprises a raster pattern of the charged particle beam; and the one or more actions comprise of adjusting a raster pattern of the charged particle beam.

Embodiment 53 is the method of any one of embodiments 47 to 52, wherein: the parameter of the neutron beam system comprises a temperature of the neutron-generating target; the cause of the difference between the symmetry measure and the expected symmetry measure comprises a uniformity of the neutron-generating target; and the one or more actions comprise at least one of adjusting a directionality of the charged particle beam or adjusting a raster pattern of the charged particle beam.

Embodiment 54 is the method of any one of embodiments 47 to 53, wherein: the parameter of the neutron beam system comprises a photon flux emitted from the neutron-generating target; the cause of the difference between the symmetry measure and the expected symmetry measure comprises a position of the patient; and the one or more actions comprise adjusting a position of a structure supporting the patient.

Embodiment 55 is the method of any one of embodiments 47 to 54, wherein: the parameter of the neutron beam system comprises a neutron flux of the neutron beam; the cause of the difference between the symmetry measure and the expected symmetry measure comprises a position of the patient; and the one or more actions comprise adjusting a position of a structure supporting the patient.

Embodiment 56 is the method of any one of embodiments 47 to 55, wherein: the parameter of the neutron beam system comprises a neutron flux of the neutron beam; the cause of the difference between the symmetry measure and the expected symmetry measure comprises a type of a collimator located between the neutron-generating target and the patient; and the one or more actions comprise adjusting the type of the collimator located between the neutron-generating target and the patient.

Embodiment 57 is the method of any one of embodiments 47 to 56, wherein: the parameter of the neutron beam system comprises a neutron flux of the neutron beam; the cause of the difference between the symmetry measure and the expected symmetry measure comprises a position of a collimator located between the neutron-generating target and the patient; and the one or more actions comprise adjusting the position of the collimator located between the neutron-generating target and the patient.

Embodiment 58 is the method of any one of embodiments 46 to 57, comprising: obtaining, from a sensor configured to monitor a parameter of a neutron beam system outputting the neutron beam, a value of the parameter; determining that a difference between the value of the parameter and an expected value of the parameter exceeds a second threshold difference; and performing the one or more actions in response to (i) determining that the difference between the symmetry measure and the expected symmetry measure exceeds the first threshold difference and (ii) determining that the difference between the value of the parameter and the expected value of the parameter exceeds the second threshold difference.

Embodiment 59 is the method of any one of embodiments 46 to 58, obtaining a measured neutron flux output by a dosimeter configured to monitor a neutron flux of a neutron beam during a boron neutron capture therapy treatment on a patient; determining a difference between the measured neutron flux and an expected neutron flux; and performing the one or more actions (i) in response to determining that the difference between the symmetry measure and the expected symmetry measure exceeds the first threshold difference and (ii) based on the difference between the measured neutron flux and the expected neutron flux.

Embodiment 60 is the method of any one of embodiments 44 to 59, wherein neutrons in the neutron beam are emitted from a neutron-generating target in response to a charged particle beam incident on the neutron-generating target.

Embodiment 61 is the method of embodiment 60, the one or more actions comprising adjusting a directionality, a focus, or a raster pattern of the charged particle beam.

Embodiment 62 is the method of any one of embodiments 60 or 61, the one or more actions comprising adjusting a setting of a high-energy beamline configured to transport the charged particle beam to the neutron-generating target.

Embodiment 63 is the method of embodiment 62, wherein adjusting the setting of the high-energy beamline comprises adjusting a field of an electromagnet of the high-energy beamline.

Embodiment 64 is the method of any one of embodiments 62 or 63, wherein adjusting the setting of the high-energy beamline comprises adjusting a focus of a quadrupole magnet of the high-energy beamline.

Embodiment 65 is the method of any one of embodiments 60 to 64, the one or more actions comprising adjusting a position of a collimator located between the neutron-generating target and the patient.

Embodiment 66 is the method of any one of embodiments 60 to 65, the one or more actions comprising adjusting a type of collimator located between the neutron-generating target and the patient.

Embodiment 67 is the method of any one of embodiments 60 to 66, comprising: obtaining, from an energy sensor, an energy of the charged particle beam; and performing the one or more actions based at least in part on the energy of the charged particle beam.

Embodiment 68 is the method of any one of embodiments 60 to 67, comprising: obtaining, from a temperature sensor, a temperature of the neutron-generating target; and performing the one or more actions based at least in part on the temperature of the neutron-generating target.

Embodiment 69 is the method of any one of embodiments 60 to 68, comprising: obtaining, from a current monitor, a current of the charged particle beam; and performing the one or more actions based at least in part on the current of the charged particle beam.

Embodiment 70 is the method of any one of embodiments 60 to 69, comprising: obtaining a measured photon flux from a photon detector configured to detect photons emitted from the neutron-generating target; and performing the one or more actions based at least in part on the measured photon flux.

Embodiment 71 is the method of any one of embodiments 60 to 70, the one or more actions comprising adjusting a setting of an accelerator configured to accelerate the charged particle beam towards the neutron-generating target.

Embodiment 72 is the method of any one of embodiments 44 to 71, wherein the patient is supported by a structure, the one or more actions comprising adjusting a position of the structure.

Embodiment 73 is the method of any one of embodiments 44 to 72, the one or more actions comprising providing a notification for presentation by a display.

Embodiment 74 is the method of any one of embodiments 44 to 73, the one or more actions comprising activating an alarm.

Embodiment 75 is the method of any one of embodiments 44 to 74, the one or more actions comprising transmitting an instruction to a neutron beam system outputting the neutron beam to cease outputting the neutron beam.

Embodiment 76 is the method of any one of embodiments 44 to 75, the one or more actions comprising adjusting a setting of a component of a neutron beam system outputting the neutron beam.

Embodiment 77 is the method of any one of embodiments 44 to 76, the one or more actions comprising adjusting at least one parameter of a beam shaping system for shaping the neutron beam.

Embodiment 78 is a non-transitory computer-readable medium storing software comprising instructions executable by one or more computers which, upon such execution, cause the one or more computers to perform operations comprising the method of any one of embodiments 44 to 77.

Embodiment 79 is a system comprising: one or more computers; and one or more storage devices storing instructions that are operable, when executed by the one or more computers, to cause the one or more computers to perform operations comprising the method of any one of embodiments 44 to 77.

Embodiment 80 is a method, comprising: performing a calibration process for a monitoring dosimeter as a first set of conditions for directing a neutron beam towards an object location, the calibration process comprising: determining the first set of conditions for directing the neutron beam to the object location, wherein neutrons in the neutron beam are emitted from a neutron-generating target in response to a charged particle beam incident on the neutron-generating target, the neutron beam propagating along an axis extending in an axial direction and having a beam radius extending in a radial direction orthogonal to the axial direction; obtaining data indicating a first neutron flux measured by the monitoring dosimeter while the neutron beam is directed towards the object location at the first set of conditions, wherein the neutron-generating target is positioned at an axial location between the monitoring dosimeter and the object location, the monitoring dosimeter being offset from the axis in the radial direction by a distance equal to or greater than the beam radius; obtaining data indicating a second neutron flux measured by a reference dosimeter while the neutron beam is directed towards the object location at the first set of conditions, wherein the reference dosimeter is positioned at an axial location between the neutron-generating target and the object location and the second neutron flux represents neutron flux incident on the object; and storing calibration data including a correlation between the first neutron flux and the second neutron flux at the first set of conditions; and based on the calibration data from the calibration process, using the monitoring dosimeter to monitor neutron flux incident on a patient during boron neutron capture therapy (BNCT) treatment.

Embodiment 81 is the method of embodiment 80, comprising performing the calibration process for the monitoring dosimeter at multiple different sets of conditions.

Embodiment 82 is the method of embodiment 81, wherein using the monitoring dosimeter to monitor neutron flux incident on the patient during BNCT treatment comprises: selecting, from the multiple different sets of conditions, a set of conditions indicative of the conditions at which the neutron beam is directed towards the patient; and determining, using a first neutron flux measured by the monitoring dosimeter and calibration data corresponding to the selected set of conditions, a second neutron flux incident on the patient.

Embodiment 83 is the method of embodiment 82, comprising: determining, based on the second neutron flux incident on the patient and a time duration of the neutron beam being directed towards the patient, that a neutron dose delivered to the patient matches or exceeds an intended neutron dose to be delivered to the patient; and in response to determining that the neutron dose delivered to the patient matches or exceeds the intended neutron dose, ceasing direction of the neutron beam towards the patient.

Embodiment 84 is the method of any one of embodiments 80 to 83, wherein the first set of conditions includes an energy of the charged particle beam.

Embodiment 85 is the method of any one of embodiments 80 to 84, wherein the first set of conditions includes a geometry of the object, the geometry of the object including at least one of a size of the object, dimensions of the object, or a distance of the object from the neutron-generating target.

Embodiment 86 is the method of any one of embodiments 80 to 85, wherein the neutron-generating target is enclosed in a neutron beam converter, the monitoring dosimeter being positioned external to the neutron beam converter on a first side of the neutron beam converter, the object location being external to the neutron beam converter on a second side of the neutron beam converter opposite from the first side.

Embodiment 87 is a method for treating a patient with boron neutron capture therapy (BNCT) under a set of conditions, the method comprising: directing a neutron beam towards a patient location, wherein neutrons in the neutron beam are emitted from a neutron-generating target in response to a charged particle beam incident on the neutron-generating target, the neutron beam propagating along an axis extending in an axial direction and having a beam radius extending in a radial direction orthogonal to the axial direction; selecting, from multiple different sets of conditions, a first set of conditions indicative of patient treatment conditions; obtaining dosimeter calibration data for the first set of conditions, the dosimeter calibration data indicating a correlation between a neutron flux measured by a monitoring dosimeter and a neutron flux directed towards the patient location, wherein the neutron-generating target is positioned at an axial location between the monitoring dosimeter and the patient location, the monitoring dosimeter being offset from the axis in the radial direction by a distance equal to or greater than the beam radius; and determining, using a neutron flux measured by the monitoring dosimeter while the neutron beam is directed towards the patient location and the dosimeter calibration data for the first set of conditions, a neutron flux incident on the patient.

Embodiment 88 is the method of embodiment 87, comprising: determining, based on the neutron flux incident on the patient and a time duration of the neutron beam being directed towards the patient, that a neutron dose delivered to the patient matches or exceeds an intended neutron dose to be delivered to the patient; and in response to determining that the neutron dose delivered to the patient matches or exceeds the intended neutron dose, ceasing to propagate the neutron beam to the patient.

Embodiment 89 is the method of any one of embodiments 87 to 88, wherein selecting, from multiple different sets of conditions, a first set of conditions indicative of patient treatment conditions comprises: selecting, from the multiple different sets of conditions, a particular set of conditions that is more similar to the patient treatment conditions than any other set of conditions of the multiple different sets of conditions, wherein determining the neutron flux incident on the patient comprises adjusting the dosimeter calibration data of the particular set of conditions to align with the patient treatment conditions.

Embodiment 90 is the method of any one of embodiments 87 to 89, wherein the first set of conditions includes at least one of an energy of the charged particle beam or geometry of the patient, the geometry of the patient including at least one of a size of the patient, dimensions of the patient, or a distance of the patient from the neutron-generating target.

Embodiment 91 is the method of any one of embodiments 87 to 90, wherein the neutron-generating target is enclosed in a neutron beam converter, the monitoring dosimeter being positioned external to the neutron beam converter on a first side of the neutron beam converter, the patient location being external to the neutron beam converter on a second side of the neutron beam converter opposite from the first side.

Embodiment 92 is a non-transitory computer-readable medium storing software comprising instructions executable by one or more computers which, upon such execution, cause the one or more computers to perform operations for treating a patient with boron neutron capture therapy (BNCT) under a set of conditions, the operations comprising: selecting, from dosimeter calibration data for multiple different sets of conditions, a first set of conditions indicative of conditions at which the patient is treated with BNCT; obtaining the dosimeter calibration data for the first set of conditions, the dosimeter calibration data indicating a correlation between a neutron flux measured by a monitoring dosimeter and a neutron flux directed towards a patient location; and determining a neutron flux incident on the patient using a neutron flux measured by the monitoring dosimeter while a neutron beam is directed towards the patient location and the dosimeter calibration data for the first set of conditions.

Embodiment 93 is a system comprising: a neutron-generating target configured to emit a neutron beam; a monitoring dosimeter; one or more computers; and one or more storage devices storing instructions that are operable, when executed by the one or more computers, to cause the one or more computers to perform operations for treating a patient with boron neutron capture therapy (BNCT) under a set of conditions, the operations comprising: selecting, from dosimeter calibration data for multiple different sets of conditions, a first set of conditions indicative of the conditions at which the patient is treated with BNCT; obtaining the dosimeter calibration data for the first set of conditions, the dosimeter calibration data indicating a correlation between a neutron flux measured by the monitoring dosimeter and a neutron flux directed towards a patient location; and determining, using a neutron flux measured by the monitoring dosimeter while the neutron beam is directed towards the patient location and the dosimeter calibration data for the first set of conditions, a neutron flux incident on the patient.

Embodiment 94 is a method, comprising: performing a calibration process for a symmetry monitoring system at a first set of conditions for directing a neutron beam towards an object location, wherein the symmetry monitoring system comprises a plurality of dosimeters and is configured to monitor symmetry of the neutron beam, the calibration process comprising: determining a first set of conditions for directing the neutron beam towards the object location, wherein neutrons in the neutron beam are emitted by a neutron-generating target in response to a charged particle beam incident on the neutron-generating target, the neutron beam propagating along an axis extending in an axial direction and having a beam radius extending in a radial direction orthogonal to the axial direction; obtaining data indicating a first neutron flux measured by a dosimeter of the symmetry monitoring system while the neutron beam is directed towards the object location at the first set of conditions, wherein the dosimeter is positioned at an axial location between the neutron-generating target and the object location, the dosimeter being offset from the axis in the radial direction by a distance equal to or less than the beam radius; obtaining data indicating a second neutron flux measured by a monitoring dosimeter while the neutron beam is directed towards the object location at the first set of conditions, wherein the neutron-generating target is positioned at an axial location between the monitoring dosimeter and the object location, the monitoring dosimeter being offset from the axis in a radial direction by a distance equal to or greater than the beam radius; and storing calibration data including a correlation between the first neutron flux and the second neutron flux at the first set of conditions; and based on the calibration data from the calibration process, using the symmetry monitoring system and the monitoring dosimeter to monitor neutron flux incident on a patient during boron neutron capture therapy (BNCT) treatment.

Embodiment 95 is the method of embodiment 94, wherein the plurality of dosimeters are arranged at different azimuthal positions around the axis of the neutron beam.

Embodiment 96 is the method of any one of embodiments 94 or 95, wherein the plurality of dosimeters are equidistant from the neutron-generating target.

Embodiment 97 is the method of any one of embodiments 94 to 96, comprising performing the calibration process for each dosimeter of the plurality of dosimeters.

Embodiment 98 is the method of any one of embodiments 94 to 97, comprising performing the calibration process for the symmetry monitoring system at multiple different sets of conditions.

Embodiment 99 is the method of any one of embodiments 94 to 98, wherein using the symmetry monitoring system and the monitoring dosimeter to monitor neutron flux incident on a patient during BNCT treatment comprises: selecting, from multiple different sets of conditions, a set of conditions indicative of the conditions at which the neutron beam is directed towards the patient; and determining, using calibration data corresponding to the selected set of conditions and a neutron flux measured by the monitoring dosimeter while the neutron beam is directed towards the patient, an expected neutron flux measured by the dosimeter of the symmetry monitoring system.

Embodiment 100 is the method of embodiment 99, wherein using the symmetry monitoring system and the monitoring dosimeter to monitor neutron flux incident on a patient during BNCT treatment comprises: determining that an error between a neutron flux measured by the dosimeter of the symmetry monitoring system and the expected neutron flux measured by the dosimeter of the symmetry monitoring system is greater than or equal to a threshold error; and in response to determining that the error between the neutron flux measured by the dosimeter of the symmetry monitoring system and the expected neutron flux measured by the dosimeter of the symmetry monitoring system is greater than or equal to the threshold error, performing one or more actions.

Embodiment 101 is the method of embodiment 100, wherein the one or more actions include providing a notification for presentation by a display.

Embodiment 102 is the method of any one of embodiments 100 or 101, wherein the one or more actions include activating an alarm.

Embodiment 103 is the method of any one of embodiments 100 to 102, wherein the one or more actions include ceasing direction of the neutron beam towards the patient.

Embodiment 104 is the method of any one of embodiments 100 to 103, wherein the one or more actions include adjusting at least one parameter of a beam shaping system for shaping the neutron beam.

Embodiment 105 is the method of any one of embodiments 94 to 104, wherein the first set of conditions includes an energy of the charged particle beam.

Embodiment 106 is the method of any one of embodiments 94 to 105, wherein the first set of conditions includes a geometry of the object, the geometry of the object including at least one of a size of the object, dimensions of the object, or a distance of the object from the neutron-generating target.

Embodiment 107 is the method of any one of embodiments 94 to 106, wherein the neutron-generating target is enclosed in a neutron beam converter, the monitoring dosimeter being positioned external to the neutron beam converter on a first side of the neutron beam converter, the object location being external to the neutron beam converter on a second side of the neutron beam converter opposite from the first side.

Embodiment 108 is a non-transitory computer-readable medium storing software comprising instructions executable by one or more computers which, upon such execution, cause the one or more computers to perform operations comprising: performing a calibration process for a symmetry monitoring system at a first set of conditions for directing a neutron beam towards an object location, wherein the symmetry monitoring system comprises a plurality of dosimeters and is configured to monitor symmetry of the neutron beam, the calibration process comprising: determining a first set of conditions for directing the neutron beam towards the object location, wherein neutrons in the neutron beam are emitted by a neutron-generating target in response to a charged particle beam incident on the neutron-generating target, the neutron beam propagating along an axis extending in an axial direction and having a beam radius extending in a radial direction orthogonal to the axial direction; obtaining data indicating a first neutron flux measured by a dosimeter of the symmetry monitoring system while the neutron beam is directed towards the object location at the first set of conditions, wherein the dosimeter is positioned at an axial location between the neutron-generating target and the object location, the dosimeter being offset from the axis in the radial direction by a distance equal to or less than the beam radius; obtaining data indicating a second neutron flux measured by a monitoring dosimeter while the neutron beam is directed towards the object location at the first set of conditions, wherein the neutron-generating target is positioned at an axial location between the monitoring dosimeter and the object location, the monitoring dosimeter being offset from the axis in a radial direction by a distance equal to or greater than the beam radius; and storing calibration data including a correlation between the first neutron flux and the second neutron flux at the first set of conditions; and based on the calibration data from the calibration process, using the symmetry monitoring system and the monitoring dosimeter to monitor neutron flux incident on a patient during boron neutron capture therapy (BNCT) treatment.

Embodiment 109 is a system comprising: a symmetry monitoring system comprising a plurality of dosimeters, wherein the symmetry monitoring system is configured to monitor symmetry of a neutron beam; a neutron-generating target; a monitoring dosimeter; one or more computers; and one or more storage devices storing instructions that are operable, when executed by the one or more computers, to cause the one or more computers to perform operations comprising: performing a calibration process for the symmetry monitoring system at a first set of conditions for directing the neutron beam towards an object location, the calibration process comprising: determining a first set of conditions for directing the neutron beam towards the object location, wherein neutrons in the neutron beam are emitted by a neutron-generating target in response to a charged particle beam incident on the neutron-generating target, the neutron beam propagating along an axis extending in an axial direction and having a beam radius extending in a radial direction orthogonal to the axial direction; obtaining data indicating a first neutron flux measured by a dosimeter of the symmetry monitoring system while the neutron beam is directed towards the object location at the first set of conditions, wherein the dosimeter is positioned at an axial location between the neutron-generating target and the object location, the dosimeter being offset from the axis in the radial direction by a distance equal to or less than the beam radius; obtaining data indicating a second neutron flux measured by the monitoring dosimeter while the neutron beam is directed towards the object location at the first set of conditions, wherein the neutron-generating target is positioned at an axial location between the monitoring dosimeter and the object location, the monitoring dosimeter being offset from the axis in a radial direction by a distance equal to or greater than the beam radius; and storing calibration data including a correlation between the first neutron flux and the second neutron flux at the first set of conditions; and based on the calibration data from the calibration process, using the symmetry monitoring system and the monitoring dosimeter to monitor neutron flux incident on a patient during boron neutron capture therapy (BNCT) treatment.

Embodiment 110 is a method for treating a patient with boron neutron capture therapy (BNCT) under a set of conditions, the method comprising: directing a neutron beam towards the patient, wherein the neutron beam is emitted by a neutron-generating target in response to a charged particle beam incident on the neutron-generating target, the neutron beam propagating along an axis extending in an axial direction and having a beam radius extending in a radial direction orthogonal to the axial direction; selecting, from multiple different sets of conditions, a first set of conditions indicative of the conditions at which the patient is treated with BNCT; obtaining dosimeter calibration data for the first set of conditions, the dosimeter calibration data indicating a correlation between a neutron flux measured by a monitoring dosimeter and a neutron flux measured by a dosimeter of a symmetry monitoring system configured to monitor symmetry of the neutron beam, wherein the neutron-generating target is positioned at an axial location between the monitoring dosimeter and the patient, the monitoring dosimeter being offset from the axis in the radial direction by a distance equal to or greater than the beam radius; determining, using the dosimeter calibration data for the first set of conditions and a neutron flux measured by the monitoring dosimeter while the neutron beam is directed towards the patient, an expected neutron flux measured by the dosimeter of the symmetry monitoring system; determining that an error between a neutron flux measured by the dosimeter of the symmetry monitoring system and the expected neutron flux measured by the dosimeter of the symmetry monitoring system is equal to or greater than a threshold error; and in response to determining that the error between the neutron flux measured by the dosimeter of the symmetry monitoring system and the expected neutron flux measured by the dosimeter of the symmetry monitoring system is equal to or greater than the threshold error, performing one or more actions.

Embodiment 111 is the method of embodiment 110, wherein the one or more actions include providing a notification for presentation by a display.

Embodiment 112 is the method of any one of embodiments 110 to 111, wherein the one or more actions include activating an alarm.

Embodiment 113 is the method of any one of embodiments 110 to 112, wherein the one or more actions include ceasing direction of the neutron beam towards the patient.

Embodiment 114 is the method of any one of embodiments 110 to 113, wherein the one or more actions include adjusting at least one parameter of a beam shaping system for shaping the neutron beam.

Embodiment 115 is the method of any one of embodiments 110 to 114, wherein selecting, from multiple different sets of conditions, a first set of conditions indicative of the conditions at which the patient is treated with BNCT comprises: selecting, from the multiple different sets of conditions, a particular set of conditions that is more similar to the conditions at which the patient is treated with BNCT than any other set of conditions of the multiple different sets of conditions.

Embodiment 116 is the method of any one of embodiments 110 to 115, wherein the first set of conditions includes at least one of an energy of the charged particle beam or a geometry of the patient, the geometry of the patient including at least one of a size of the patient, dimensions of the patient, or a distance of the patient from the neutron-generating target.

Embodiment 117 is the method of any one of embodiments 110 to 116, wherein the neutron-generating target is enclosed in a neutron beam converter, the monitoring dosimeter being positioned external to the neutron beam converter on a first side of the neutron beam converter, the patient being located external to the neutron beam converter on a second side of the neutron beam converter opposite from the first side.

Embodiment 118 is a non-transitory computer-readable medium storing software comprising instructions executable by one or more computers which, upon such execution, cause the one or more computers to perform operations for treating a patient with boron neutron capture therapy (BNCT) under a set of conditions, the operations comprising: storing dosimeter calibration data for multiple different sets of conditions; directing a neutron beam towards the patient, wherein the neutron beam is emitted by a neutron-generating target in response to a charged particle beam incident on the neutron-generating target, the neutron beam propagating along an axis extending in an axial direction and having a beam radius extending in a radial direction orthogonal to the axial direction; selecting, from multiple different sets of conditions, a first set of conditions indicative of the conditions at which the patient is treated with BNCT; obtaining the dosimeter calibration data for the first set of conditions, the dosimeter calibration data indicating a correlation between a neutron flux measured by a monitoring dosimeter and a neutron flux measured by a dosimeter of a symmetry monitoring system configured to monitor symmetry of the neutron beam, wherein the neutron-generating target is positioned at an axial location between the monitoring dosimeter and the patient, the monitoring dosimeter being offset from the axis in the radial direction by a distance equal to or greater than the beam radius; determining, using the dosimeter calibration data for the first set of conditions and a neutron flux measured by the monitoring dosimeter while the neutron beam is directed towards the patient, an expected neutron flux measured by the dosimeter of the symmetry monitoring system; determining that an error between a neutron flux measured by the dosimeter of the symmetry monitoring system and the expected neutron flux measured by the dosimeter of the symmetry monitoring system is equal to or greater than a threshold error; and in response to determining that the error between the neutron flux measured by the dosimeter of the symmetry monitoring system and the expected neutron flux measured by the dosimeter of the symmetry monitoring system is equal to or greater than the threshold error, performing one or more actions.

Embodiment 119 is a system comprising: a neutron-generating target configured to emit a neutron beam; a monitoring dosimeter; a symmetry monitoring system comprising a plurality of dosimeters, wherein the symmetry monitoring system is configured to monitor symmetry of the neutron beam; one or more computers; and one or more storage devices storing instructions that are operable, when executed by the one or more computers, to cause the one or more computers to perform operations for treating a patient with boron neutron capture therapy (BNCT) under a set of conditions, the operations comprising: storing dosimeter calibration data for multiple different sets of conditions; directing the neutron beam towards the patient, wherein the neutron beam is emitted by the neutron-generating target in response to a charged particle beam incident on the neutron-generating target, the neutron beam propagating along an axis extending in an axial direction and having a beam radius extending in a radial direction orthogonal to the axial direction; selecting, from multiple different sets of conditions, a first set of conditions indicative of the conditions at which the patient is treated with BNCT; obtaining the dosimeter calibration data for the first set of conditions, the dosimeter calibration data indicating a correlation between a neutron flux measured by the monitoring dosimeter and a neutron flux measured by a dosimeter of the symmetry monitoring system configured to monitor symmetry of the neutron beam, wherein the neutron-generating target is positioned at an axial location between the monitoring dosimeter and the patient, the monitoring dosimeter being offset from the axis in the radial direction by a distance equal to or greater than the beam radius; determining, using the dosimeter calibration data for the first set of conditions and a neutron flux measured by the monitoring dosimeter while the neutron beam is directed towards the patient, an expected neutron flux measured by the dosimeter of the symmetry monitoring system; determining that an error between a neutron flux measured by the dosimeter of the symmetry monitoring system and the expected neutron flux measured by the dosimeter of the symmetry monitoring system is equal to or greater than a threshold error; and in response to determining that the error between the neutron flux measured by the dosimeter of the symmetry monitoring system and the expected neutron flux measured by the dosimeter of the symmetry monitoring system is equal to or greater than the threshold error, performing one or more actions.

Embodiment 120 is a method, comprising: propagating a neutron beam along a beam path from a target to an object; obtaining a first neutron flux of the neutron beam with a monitoring dosimeter and a second neutron flux of the neutron beam with a reference dosimeter, wherein the reference dosimeter is located along the beam path and the monitoring dosimeter is offset from the beam path; and determining calibration data indicative of a correlation between the first neutron flux and the second neutron flux.

Embodiment 121 is the method of embodiment 120, wherein the neutron beam is generated by the target in response to a charged particle beam incident on the target.

Embodiment 122 is the method of any one of embodiments 120 or 121, comprising using the monitoring dosimeter and the calibration data to monitor neutron flux incident on a patient during boron neutron capture therapy (BNCT) treatment.

Embodiment 123 is the method of any one of embodiments 120 to 122, wherein using the monitoring dosimeter to monitor neutron flux incident on the patient during BNCT treatment comprises: selecting, from multiple different sets of conditions, a set of conditions indicative of the conditions at which the neutron beam is directed towards the patient; and determining, using a first neutron flux measured by the monitoring dosimeter and calibration data corresponding to the selected set of conditions, a second neutron flux incident on the patient.

Embodiment 124 is a non-transitory computer-readable medium storing software comprising instructions executable by one or more computers which, upon such execution, cause the one or more computers to perform operations comprising: obtaining a first neutron flux of a neutron beam with a monitoring dosimeter and a second neutron flux of the neutron beam with a reference dosimeter, wherein the reference dosimeter is located along a beam path of the neutron beam and the monitoring dosimeter is offset from the beam path; and determining calibration data indicative of a correlation between the first neutron flux and the second neutron flux.

Embodiment 125 is a system comprising: one or more computers; and one or more storage devices storing instructions that are operable, when executed by the one or more computers, to cause the one or more computers to perform operations comprising: obtaining a first neutron flux of a neutron beam with a monitoring dosimeter and a second neutron flux of the neutron beam with a reference dosimeter, wherein the reference dosimeter is located along a beam path of the neutron beam and the monitoring dosimeter is offset from the beam path; and determining calibration data indicative of a correlation between the first neutron flux and the second neutron flux.

Embodiment 126 is a method, comprising: monitoring a first neutron flux of a neutron beam with a monitoring dosimeter during a boron neutron capture therapy (BNCT) treatment on a patient, wherein the neutron beam is generated by a target and the monitoring dosimeter is offset from a beam path from the target to the patient; and determining neutron flux incident on the patient using calibration data indicative of a correlation between the first neutron flux and neutron flux along the beam path.

Embodiment 127 is the method of embodiment 126, comprising: storing sets of calibration data for multiple sets of conditions; and selecting, from the multiple sets of conditions, a first set of conditions indicative of the conditions at which the patient is treated with BNCT; and determining the neutron flux incident on the patient using calibration data for the first set of conditions.

Embodiment 128 is the method of any one of embodiments 126 or 127, comprising: determining, based on the neutron flux incident on the patient and a time duration of the treatment, that a neutron dose delivered to the patient matches or exceeds an intended neutron dose to be delivered to the patient; and in response, ceasing treatment on the patient.

Embodiment 129 is the method of any one of embodiments 126 to 128, wherein the neutron beam is generated by the target in response to a charged particle beam incident on the target, the first set of conditions including an energy of a charged particle beam.

Embodiment 130 is the method of any one of embodiments 126 to 129, wherein the first set of conditions includes a geometry of the patient, the geometry of the patient including at least one of a size of the patient, dimensions of the patient, or a distance of the patient from the target.

Embodiment 131 is a non-transitory computer-readable medium storing software comprising instructions executable by one or more computers which, upon such execution, cause the one or more computers to perform operations comprising: monitoring a first neutron flux of a neutron beam with a monitoring dosimeter during a boron neutron capture therapy (BNCT) treatment on a patient, wherein the neutron beam is generated by a target and the monitoring dosimeter is offset from a beam path from the target to the patient; and determining neutron flux incident on the patient using calibration data indicative of a correlation between the first neutron flux and neutron flux along the beam path.

Embodiment 132 is a system comprising: one or more computers; and one or more storage devices storing instructions that are operable, when executed by the one or more computers, to cause the one or more computers to perform operations comprising: monitoring a first neutron flux of a neutron beam with a monitoring dosimeter during a boron neutron capture therapy (BNCT) treatment on a patient, wherein the neutron beam is generated by a target and the monitoring dosimeter is offset from a beam path from the target to the patient; and determining neutron flux incident on the patient using calibration data indicative of a correlation between the first neutron flux and neutron flux along the beam path.

Embodiment 133 is a method, comprising: propagating a neutron beam along a beam path from a target to an object; obtaining a first neutron flux of the neutron beam with a dosimeter of a symmetry monitoring system and a second neutron flux of the neutron beam with a monitoring dosimeter, wherein the symmetry monitoring system is located along the beam path and the monitoring dosimeter is offset from the beam path; and determining calibration data indicative of a correlation between the first neutron flux and the second neutron flux.

Embodiment 134 is the method of embodiment 133, wherein the symmetry monitoring system comprises a plurality of dosimeters and is configured to monitor symmetry of the neutron beam.

Embodiment 135 is the method of embodiment 134, wherein the plurality of dosimeters are arranged at different azimuthal positions around an axis of the neutron beam.

Embodiment 136 is the method of any one of embodiments 134 or 135, wherein the plurality of dosimeters are equidistant from the target.

Embodiment 137 is the method of any one of embodiments 133 to 136, comprising using the symmetry monitoring system and the calibration data to monitor neutron flux incident on a patient during boron neutron capture therapy (BNCT) treatment.

Embodiment 138 is the method of embodiment 137, wherein using the symmetry monitoring system and the calibration data to monitor neutron flux incident on the patient during BNCT treatment comprises: selecting, from multiple different sets of conditions, a set of conditions indicative of the conditions at which the neutron beam is directed towards the patient; and determining, using calibration data corresponding to the selected set of conditions and a neutron flux measured by the monitoring dosimeter while the neutron beam is directed towards the patient, an expected neutron flux measured by the dosimeter of the symmetry monitoring system.

Embodiment 139 is the method of embodiment 138, wherein using the symmetry monitoring system and the calibration data to monitor neutron flux incident on the patient during BNCT treatment comprises: in response to determining that an error between a neutron flux measured by the dosimeter of the symmetry monitoring system and the expected neutron flux measured by the dosimeter of the symmetry monitoring system is greater than or equal to a threshold error, performing one or more actions.

Embodiment 140 is a non-transitory computer-readable medium storing software comprising instructions executable by one or more computers which, upon such execution, cause the one or more computers to perform operations comprising: obtaining a first neutron flux of a neutron beam with a dosimeter of a symmetry monitoring system and a second neutron flux of a neutron beam with a monitoring dosimeter, wherein the symmetry monitoring system is located along a beam path from a target to an object, and the monitoring dosimeter is offset from the beam path; and determining calibration data indicative of a correlation between the first neutron flux and the second neutron flux.

Embodiment 141 is a system comprising: one or more computers; and one or more storage devices storing instructions that are operable, when executed by the one or more computers, to cause the one or more computers to perform operations comprising: obtaining a first neutron flux of a neutron beam with a dosimeter of a symmetry monitoring system and a second neutron flux of the neutron beam with a monitoring dosimeter, wherein the symmetry monitoring system is located along a beam path from a target to an object, and the monitoring dosimeter is offset from the beam path; and determining calibration data indicative of a correlation between the first neutron flux and the second neutron flux.

Embodiment 142 is a method comprising: determining an expected neutron flux measured by a dosimeter of a symmetry monitoring system configured to monitor symmetry of a neutron beam propagating along a beam path from a target to an object; determining an error between a neutron flux measured by the dosimeter of the symmetry monitoring system and the expected neutron flux; and in response to determining that the error between the neutron flux measured by the dosimeter of the symmetry monitoring system and the expected neutron flux is equal to or greater than a threshold error, performing one or more actions.

Embodiment 143 is the method of embodiment 142, wherein determining the expected neutron flux measured by the dosimeter of a symmetry monitoring system comprises simulating neutron reflection from the object.

Embodiment 144 is the method of embodiment 143, wherein simulating neutron reflection from the object comprises performing a Monte Carlo simulation of neutron reflection from the object.

Embodiment 145 is the method of any one of embodiments 142 to 144, comprising: determining the expected neutron flux measured by the dosimeter of a symmetry monitoring system based on dosimeter calibration data indicating a correlation between a neutron flux measured by a monitoring dosimeter and a neutron flux measured by the dosimeter of the symmetry monitoring system, wherein the symmetry monitoring system is located along the beam path and the monitoring dosimeter is offset from the beam path.

Embodiment 146 is the method of any one of embodiments 142 to 145, wherein the one or more actions include providing a notification for presentation by a display.

Embodiment 147 is the method of any one of embodiments 142 to 146, wherein the one or more actions include activating an alarm.

Embodiment 148 is the method of any one of embodiments 142 to 147, wherein the one or more actions include ceasing propagation of the neutron beam.

Embodiment 149 is the method of any one of embodiments 142 to 148, wherein the one or more actions include adjusting at least one parameter of a beam shaping system for shaping the neutron beam.

Embodiment 150 is a non-transitory computer-readable medium storing software comprising instructions executable by one or more computers which, upon such execution, cause the one or more computers to perform operations comprising: determining an expected neutron flux measured by a dosimeter of a symmetry monitoring system configured to monitor symmetry of a neutron beam propagating along a beam path from a target to an object; determining an error between a neutron flux measured by the dosimeter of the symmetry monitoring system and the expected neutron flux; and in response to determining that the error between the neutron flux measured by the dosimeter of the symmetry monitoring system and the expected neutron flux is equal to or greater than a threshold error, performing one or more steps.

Embodiment 151 is a system comprising: one or more computers; and one or more storage devices storing instructions that are operable, when executed by the one or more computers, to cause the one or more computers to perform operations comprising: determining an expected neutron flux measured by a dosimeter of a symmetry monitoring system configured to monitor symmetry of a neutron beam propagating along a beam path from a target to an object;

determining an error between a neutron flux measured by the dosimeter of the symmetry monitoring system and the expected neutron flux; and in response to determining that the error between the neutron flux measured by the dosimeter of the symmetry monitoring system and the expected neutron flux is equal to or greater than a threshold error, performing one or more steps.

Embodiment 152 is a non-transitory computer-readable medium storing software comprising instructions executable by one or more computers which, upon such execution, cause the one or more computers to perform operations comprising: performing a calibration process for a monitoring dosimeter at a first set of conditions for directing a neutron beam towards an object location, the calibration process comprising: determining the first set of conditions for directing the neutron beam to the object location, wherein neutrons in the neutron beam are emitted from a neutron-generating target in response to a charged particle beam incident on the neutron-generating target, the neutron beam propagating along an axis extending in an axial direction and having a beam radius extending in a radial direction orthogonal to the axial direction; obtaining data indicating a first neutron flux measured by the monitoring dosimeter while the neutron beam is directed towards the object location at the first set of conditions, wherein the neutron-generating target is positioned at an axial location between the monitoring dosimeter and the object location, the monitoring dosimeter being offset from the axis in the radial direction by a distance equal to or greater than the beam radius; obtaining data indicating a second neutron flux measured by a reference dosimeter while the neutron beam is directed towards the object location at the first set of conditions, wherein the reference dosimeter is positioned at an axial location between the neutron-generating target and the object location and the second neutron flux represents neutron flux incident on the object; and storing calibration data including a correlation between the first neutron flux and the second neutron flux at the first set of conditions; and based on the calibration data from the calibration process, using the monitoring dosimeter to monitor neutron flux incident on a patient during boron neutron capture therapy (BNCT) treatment.

Embodiment 153 is a system comprising: a neutron-generating target configured to emit a neutron beam; a monitoring dosimeter; one or more computers; and one or more storage devices storing instructions that are operable, when executed by the one or more computers, to cause the one or more computers to perform operations comprising: performing a calibration process for the monitoring dosimeter at a first set of conditions for directing the neutron beam towards an object location, the calibration process comprising: determining the first set of conditions for directing the neutron beam to the object location, wherein neutrons in the neutron beam are emitted from the neutron-generating target in response to a charged particle beam incident on the neutron-generating target, the neutron beam propagating along an axis extending in an axial direction and having a beam radius extending in a radial direction orthogonal to the axial direction; obtaining data indicating a first neutron flux measured by the monitoring dosimeter while the neutron beam is directed towards the object location at the first set of conditions, wherein the neutron-generating target is positioned at an axial location between the monitoring dosimeter and the object location, the monitoring dosimeter being offset from the axis in the radial direction by a distance equal to or greater than the beam radius; obtaining data indicating a second neutron flux measured by a reference dosimeter while the neutron beam is directed towards the object location at the first set of conditions, wherein the reference dosimeter is positioned at an axial location between the neutron-generating target and the object location and the second neutron flux represents neutron flux incident on the object; and storing calibration data including a correlation between the first neutron flux and the second neutron flux at the first set of conditions; and based on the calibration data from the calibration process, using the monitoring dosimeter to monitor neutron flux incident on a patient during boron neutron capture therapy (BNCT) treatment.

Embodiment 154 is a system comprising: a neutron-generating target configured to emit a neutron beam; a monitoring dosimeter; and a symmetry monitoring system comprising a plurality of dosimeters, wherein the symmetry monitoring system is configured to monitor symmetry of the neutron beam.

Embodiment 155 is the system of embodiment 154, further comprising: an ion source configured to generate an ion beam; and a tandem accelerator configured to accelerate the ion beam, convert the ion beam to a proton beam, and accelerate the proton beam towards the neutron-generating target.

Embodiment 156 is the system of embodiment 155, wherein the neutron-generating target comprises a lithium layer.

Embodiment 157 is a system comprising: a neutron-generating target configured to emit a neutron beam along a beam path to an object; a monitoring dosimeter located in a position offset from the beam path; and a reference dosimeter located on the beam path.

Embodiment 158 is the system of embodiment 157, further comprising: an ion source configured to generate an ion beam; and a tandem accelerator configured to accelerate the ion beam, convert the ion beam to a proton beam, and accelerate the proton beam towards the neutron-generating target.

Embodiment 159 is the system of any one of embodiments 157 or 158, wherein the neutron-generating target comprises a lithium layer.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

As used herein, the term "real-time" can refer to transmitting or processing data without intentional delay given the processing limitations of a system, the time required to accurately obtain data, and the rate of change of the data. Although there may be some actual delays, the delays are generally imperceptible to a user. Real-time monitoring of neutrons can include a delay between neutron emission and dose determination of one second or less (e.g., a delay of 0.5 seconds or less, 0.1 seconds or less, 0.05 seconds or less).

The term "real-time" can refer to performing actions without intentional delay given the processing limitations of a system, the time required to accurately analyze data, and time required to generate a control signal to perform the actions. Real-time performance of an action can include a delay between detection of a condition and initiation of the action of ten seconds or less (e.g., a delay of five seconds or less, three seconds or less, one second or less).

A number of implementations have been described. Nevertheless, it will be understood that various modifications may be made without departing from the spirit and scope of the disclosure. For example, various forms of the flows shown above may be used, with steps re-ordered, added, or removed. Actions of the disclosed methods can be performed in any order, and may be performed simultaneously. Accordingly, other implementations are within the scope of the following claims.

What is claimed is:

1. A method, comprising:

obtaining a measured neutron flux output by a dosimeter configured to monitor a neutron flux of a neutron beam during a boron neutron capture therapy (BNCT) treatment on a patient, wherein neutrons in the neutron beam are emitted from a neutron-generating target in response to a charged particle beam incident on the neutron-generating target;

determining an expected neutron flux based on an energy of the charged particle beam; and in response to determining that a difference between the measured neutron flux and the expected neutron flux exceeds a first threshold difference, performing one or more actions, wherein performing the one or more actions comprises adjusting a duration of the boron neutron capture therapy (BNCT) treatment based on the difference between the measured neutron flux and the expected neutron flux.

2. The method of claim 1, comprising:

determining, based on the measured neutron flux, that a neutron dose delivered to the patient matches or exceeds an intended neutron dose to be delivered to the patient; and in response to determining that the neutron dose delivered to the patient matches or exceeds the intended neutron dose, transmitting an instruction to a neutron beam system outputting the neutron beam to cease outputting the neutron beam.

3. The method of claim 1, comprising:

determining the expected neutron flux based on a current of the charged particle beam.

4. The method of claim 1, further comprising:

obtaining sensor data from a sensor configured to monitor a parameter of a neutron beam system outputting the neutron beam;

determining, using the sensor data, a cause of the difference between the measured neutron flux and the expected neutron flux; and performing the one or more actions based on the cause of the difference between the measured neutron flux and the expected neutron flux.

5. The method of claim 4, wherein the parameter is selected from the group consisting of:

a current of the charged particle beam;

an energy of the charged particle beam;

a temperature of the neutron-generating target;

a photon flux emitted from the neutron-generating target; and a symmetry of the neutron beam.

6. The method of claim 4, wherein the cause of the difference between the measured neutron flux and the expected neutron flux comprises one of the group consisting of:

an energy of an accelerator configured to accelerate the charged particle beam towards the neutron-generating target;

a directionality of the charged particle beam;

a focus of the charged particle beam;

a raster pattern of the charged particle beam;

a thickness of the neutron-generating target;

a type of a collimator located between the neutron-generating target and the patient;

a position of the collimator located between the neutron-generating target and the patient; and a position of the patient.

7. The method of claim 4, wherein the one or more actions is selected from the group consisting of:

adjusting an energy of an accelerator configured to accelerate the charged particle beam towards the neutron-generating target;

adjusting a directionality of the charged particle beam;

adjusting a focus of the charged particle beam;

adjusting a raster pattern of the charged particle beam;

adjusting a type of a collimator located between the neutron-generating target and the patient;

adjusting a position of the collimator located between the neutron-generating target and the patient; and adjusting a position of a structure supporting the patient.

8. The method of claim 4, wherein:

the parameter of the neutron beam system comprises a current of the charged particle beam or an energy of the charged particle beam;

the cause of the difference between the measured neutron flux and the expected neutron flux comprises a setting of an accelerator configured to accelerate the charged particle beam; and the one or more actions comprise adjusting the setting of the accelerator.

9. The method of claim 4, wherein:

the parameter of the neutron beam system comprises a temperature of the neutron-generating target;

the cause of the difference between the measured neutron flux and the expected neutron flux comprises a directionality of the charged particle beam; and the one or more actions comprise adjusting the directionality of the charged particle beam.

10. The method of claim 4, wherein:

the parameter of the neutron beam system comprises a temperature of the neutron-generating target;

the cause of the difference between the measured neutron flux and the expected neutron flux comprises a focus of the charged particle beam; and the one or more actions comprise adjusting the focus of the charged particle beam.

11. The method of claim 4, wherein:

the parameter of the neutron beam system comprises a temperature of the neutron-generating target;

the cause of the difference between the measured neutron flux and the expected neutron flux comprises a raster pattern of the charged particle beam; and the one or more actions comprise of adjusting the raster pattern of the charged particle beam.

12. The method of claim 4, wherein:

the parameter of the neutron beam system comprises a temperature of the neutron-generating target;

the cause of the difference between the measured neutron flux and the expected neutron flux comprises a thickness of the neutron-generating target; and the one or more actions comprise at least one of adjusting a directionality of the charged particle beam, adjusting a focus of the charged particle beam, or adjusting a raster pattern of the charged particle beam.

13. The method of claim 4, wherein:

the parameter of the neutron beam system comprises a photon flux emitted from the neutron-generating target;

the cause of the difference between the measured neutron flux and the expected neutron flux comprises a setting of an accelerator configured to accelerate the charged particle beam; and the one or more actions comprise adjusting the setting of the accelerator.

14. The method of claim 4, wherein:

the parameter of the neutron beam system comprises a symmetry of the neutron beam;

the cause of the difference between the measured neutron flux and the expected neutron flux comprises a position of the patient; and the one or more actions comprise adjusting a position of a structure supporting the patient.

15. The method of claim 4, wherein:

the parameter of the neutron beam system comprises a symmetry of the neutron beam;

the cause of the difference between the measured neutron flux and the expected neutron flux comprises a type of a collimator located between the neutron-generating target and the patient; and the one or more actions comprise adjusting the type of the collimator located between the neutron-generating target and the patient.

16. The method of claim 4, wherein:

the parameter of the neutron beam system comprises a symmetry of the neutron beam;

the cause of the difference between the measured neutron flux and the expected neutron flux comprises a position of a collimator located between the neutron-generating target and the patient; and the one or more actions comprise adjusting the position of the collimator located between the neutron-generating target and the patient.

\* \* \* \* \*